US006803231B1

(12) United States Patent
Blaser et al.

(10) Patent No.: US 6,803,231 B1
(45) Date of Patent: Oct. 12, 2004

(54) METHOD OF DELIVERING ANTIGENS FOR VACCINATION WITH A LIVE VECTOR

(75) Inventors: Martin Blaser, Nashville, TN (US); Joel Dworkin, Kirkwood, MO (US); Stuart A. Thompson, Evans, GA (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/355,793

(22) PCT Filed: Jan. 30, 1998

(86) PCT No.: PCT/US98/01780

§ 371 (c)(1),
(2), (4) Date: Sep. 21, 1999

(87) PCT Pub. No.: WO98/33386

PCT Pub. Date: Aug. 6, 1998

(51) Int. Cl.[7] .................... A01N 63/00; A61K 48/00; C07H 21/02

(52) U.S. Cl. .................... 435/325; 435/348; 435/362; 435/365; 435/367; 435/252.3; 435/252.33; 435/252.31; 435/254.2; 435/254.21; 435/320.1; 435/69.1; 536/23.7; 424/164.1

(58) Field of Search ................ 435/325, 348, 435/362, 365, 367, 252.3, 252.33, 252.31, 254.2, 254.21, 320.1, 69.1, 252.2, 254.1, 69.3, 252.1; 536/23.7; 424/164.1, 236.1, 184.1, 92, 200.1; 530/350; 514/44

(56) References Cited

U.S. PATENT DOCUMENTS 5,043,158 A * 8/1991 Sleytr et al. .................. 424/92
5,470,573 A * 11/1995 Lubitz et al. ............. 424/200.1
5,679,564 A * 10/1997 Pace et al. ................ 435/252.1

OTHER PUBLICATIONS

Fujita, M et al, Archives of Microbiology, vol. 164(6), Dec., pp. 444–447, Dec. 1995.*
Dworkin, J et al, Mol. Microbiol., vol. 19(6), pp. 1241–1253, (abstract), Mar. 1996.*
Dworkin, J et al, J. Biol. Chem., vol. 270(25), pp. 15093–15101, (abstract), Jun. 1995.*
Blaser et al, Mol. Microbiol, vol. 14(3), pp. 453–462, (abstract), Nov. 1994.*
Wang, E et al, J. Bacteriol. vol. 175(6), pp. 4979–4984, Aug. 1993.*
Tummuru, MK et al, Proc Natl Acad Sce, Aug. 1, vol. 90(15), (abstract), Aug. 1993.*
Blaser, MJ, Am. J Med. Sci, Nov., vol. 306(5), pp. 325–329, Nov. 1993.*
Szostak et al, J Biotechnology, vol. 44, pp. 161–170, 1996.*
Szotak et al, Behring Inst. Mitt, No. 98, pp. 191–196, 1997.*
Grogono–Thomas et al, FEMS Microbiolog. Review, vol. 20(1–2), Jun., pp. 99–149, Jun. 1997.*
Yang et al, J. Bacteriol, vol. 174(4), pp. 1258–1267, (abstract), Feb. 1992.*

(List continued on next page.)

Primary Examiner—Lynette R. F. Smith
Assistant Examiner—Ginny Allen Portner
(74) Attorney, Agent, or Firm—Benjamin Aaron Adler

(57) ABSTRACT

The present invention provides a mutant C. fetus strain in which one or more sapA homologs are altered by an inserted DNA cassette so that the encoded S-layer proteins represent a chimera between the native S-layer proteins and a heterologous peptide encoded by the inserted cassette. Preferably, the heterologous peptide is an immunogen of a pathogen and the mutant strain can be used to immunize a host to develop mucosal and systemic immune responses to such immunogen.

11 Claims, 11 Drawing Sheets

OTHER PUBLICATIONS

Boot, HJ et al, Mol. Microbiol, vol. 21(6), pp. 11117–1123, Sep. 1996.*

Salama, et al , FEMS Microbiol. Letters, vol. 132(3), pp. 239–245, 1995.*

Dworkin, J et al, Abstr Gen Meet Am Soc Microbiol, vol. 93(0), p. 129, (abstract), 1993.*

Blaser, MJ et al, J Biological Chem., vol. 265(24), pp. 14529–14535, 1990.*

Blaser, MJ et al, J Cellular Biochemistry, Suppl., vol. 0 (18 part A), p. 40 (abstract), 1994.*

Dworkin, J et aL, J. Bacteriology, vol. 177(7), pp. 1734–1741, Dec. 1995.*

Salama, SM et al, FEMS Microbiol. Lett, Oct. 15, 1995, vol. 132(3), pp. 239–245.*

Baszczynski et al, Biochemistry and Cell Biology, vol. 68(6), pp. 983–987, Jun. 1990 (abstract only), Jun. 1990.*

Watanabe, H et al, analyst, vol. 124(11), pp. 1611–1615, Nov. 1999 (abstract only), Nov. 1999.*

Tummuru, MK et al, Proceedings of the National Academy of Sciences of the United States of America, vol. 90(15), pp. 7265–7269, Aug. 1, 1993 (abstract only), Aug. 1993.*

Dworkin, J et al, Journal of Bacteriology, Dec. 1997, vol. 179(23) pp. 7523–7529, (abstract only), Dec. 1997.*

Thompson, SA et al, Journal of Bacteriology, vol. 180(24), pp. 6450–6458, Dec. 1998, Dec. 1998.*

Garcia, MM et al, Journal of Bacteriology, vol. 177(8), pp. 1976–1980, Apr. 1995, (abstract only), Apr. 1995.*

Blaser, MJ et al, J. Cellular Biochemistry, Suppl. vol.. 0 (18 part A), p. 40, abstract, 1994.*

Blaser, MJ et al, Am. J. Medical Science. Nov., vol. 306(5), pp. 325–329, Nov. 1993.*

Blaser, MJ et al, J. of Biological Chemistry, vol. 265(24), pp. 14529–14535, 1990.*

Blaser, MJ et al, Mol. Microbiology, vol. 14(3), Nov. 1994, pp. 453–462.*

Boot, HJ e al, Molecular Microbiology, vol. 21(6), pp. 1117–1123, Sep. 1996.*

Dworkin, J et al, Molecular Microbiology, Voo. 19(6), Mar. 1996, pp. 1241–1253.*

Dworkin, J et al, J of Bacteriology, vol. 177(7), pp. 1734–1741, Apr. 1995.*

Dworkin, J et al, 93rd General Meeting of the Am. Soc. for Microbiology, May 16–20, Ab. Gen Meet. Am. Soc. Microbiol. vol. 93(0), p. 129, abstract, D–193.*

Dworkin, J et al, J Biological Chemistry, vol. 270(25), Jun. 23, 1995, apges 15093–15101.*

Dworkin, J et al, J Bacteriology, Dec. 1997, vol. 179(23), pp. 7523–7529.*

Guerry, P et al, Infection and Immunity, Voo. 62(2), pp. 426–432, Feb. 1994, Development and characterization of recA mutants of Campylobacter jejuni for inclusion in attenuated vaccines.*

Reeck, GR et al, Cell, Voo.I 50, pate 667, Aug. 28, 1987.*

Lewin, Roger, Science, vol. 237, p. 1570, 1987 When does homology mean something eles?.*

* cited by examiner

METHOD OF DELIVERING ANTIGENS FOR VACCINATION WITH A LIVE VECTOR

CROSS-REFERENCE TO RELATED APPLICATION

This patent application claims benefit of priority under 35 U.S.C. 119 of PCT/US98/01780 filed Jan. 30, 1998, which claims benefit of provisional patent application U.S. Ser. No. 60/036,321 filed Jan. 31, 1997, now abandoned.

FEDERAL FUNDING LEGEND

This invention was supported in part under grant RO1-AI24145 from the National Institutes of Health. Accordingly, the United States government has certain rights in this invention.

BACKGROUND OF THE INVENTION

1. Field of the Invention

The present invention relates generally to the fields of immunology and vaccine technology. More specifically, the present invention relates to methods of delivering antigens for vaccination with a live vector.

2. Description of the Related Art

One way in which microorganisms can alter their surface properties, allowing a fraction of the population to preadapt to environmental changes, is by varying protein expression through programmed genomic DNA rearrangements (1). Phase, antigenic, or size variation of expressed surface proteins are governed by mechanisms including transposition and DNA inversion. During transposition, a silent gene is activated by movement to an expression site where it displaces the currently expressed gene. In DNA inversion, a segment of DNA is cut, inverted, and then rejoined by a site-specific recombinase. The invertible DNA segment may contain either a promoter that directs expression of fixed structural genes or structural genes controlled by a fixed promoter. Transposition and inversion differ in both the enzymes used and in the number of genes that can be controlled (many versus two).

*Campylobacter fetus*, a bacterial pathogen of ungulates and humans, is covered by a paracrystalline surface (S-) layer, composed of high molecular weight S-layer proteins (SLP) that masks most of the underlying gram-negative surface features (2). More than 300 bacterial genera have been described that possess S-layers (3). The S-layer renders *C. fetus* cells resistant to serum killing by prohibiting the binding of C3b (4), and the S-layer proteins themselves may change, permitting antigenic variation (5,6).

These S-layer proteins are encoded by 7–9 tightly clustered and partially homologous promoterless gene cassettes (7,8). Since previous studies show that *C. fetus* can express alternative S-layer proteins (4–6,9), there is only a single promoter for S-layer proteins expression present on a 6.2 kb invertible element (9), and the structural genes flanking the promoter are subject to substitution (9), both the promoter and the eight structural genes (sapA and its homologs) may rearrange strictly by inversion.

*Campylobacter fetus* is able to colonize the mucosa of the gastrointestinal and/or genitourinary tracts of mammals, birds and reptiles. Colonization of the wild-type organism lasts for years and can cause disease. Essential for this long term colonization is the ability to produce the S-layer proteins and *Campylobacter fetus* has the means to change the S-layer proteins and thus the crystal struture and the particular forms of antigenicity. This antigenic variation is required for the persistence of the organism in its environmental niche.

*Campylobacter fetus* accomplishes this antigenic variation by posssessing 7–9 highly homologous gene cassettes, called sapA homologs (sapA, sapA1, sapA2, etc.) which encode a different S-layer protein. Each of these homologs contains a 5' region of about 600 base pairs which is completely conserved from homolog to homolog and is necessary for binding of the S-layer protein encoded by that homolog to the lipopolysaccharide molecule anchored in the bacterial outer membrane. The remainder of the open reading frame (ORF) is different for each homolog but semi-conserved regions exist. Wild type *C. fetus* strains are able to rearrange their chromosomal DNA so that the sapA homolog positioned downstream of a unique promoter is then expressed. This rearrangement occurs at a frequency of about $10^{-4}$ and is recA dependent. RecA is a protein encoded by recA and which is involved in homologous recombination and in repair of breaks of DNA strands.

*C. fetus* S-layer proteins (SLPs) are secreted in the absence of an N-terminal signal sequence. SLP proteins contain a signal sequence located within the C-terminous of the protein and are secreted through a type I protein secretion system encoded by the sapCDEF operon of four overlapping genes. Analysis of the C-termini of four *C. fetus* SLPs revealed conserved structures that are potential secretion signals. A *C. fetus* sapD mutant neither produced nor secreted SLPs. *E. coli* expressing *C. fetus* sapA and sapCDEF secreted SapA, indicating that the sapCDEF genes were sufficient for SLP secretion.

The prior art is deficient in the lack of effective means of delivering antigens for vaccination with a live vector. The present invention fulfills this longstanding need and desire in the art.

SUMMARY OF THE INVENTION

In one embodiment of the present invention, there is provided a mutant *C. fetus* strain in which each of the cassettes is replaced by a heterologous antigen. The sapA homologs are altered by a DNA cassette inserted so that the encoded SLP represents a chimera between the native SLP and the peptide encoded by the cassette. The inserted DNA cassettes retain 3' sapA sequences that encode the C-terminal secretion signal sequences in order to ensure secretion of the chimeric protein. Representative examples of cassettes that can be inserted in this fashion include immunogens related to Salmonella, *Campylobacter jejuni*, *E. coli* 0157:H7, human immunodeficiency virus (HIV), simian immunodeficiency virus (SIV) as well as other enteric, venereal, or respiratory pathogens of humans, cattle, sheep, poultry, horses, swine, and reptiles. In this embodiment of the present invention, this strain can be used to immunize a host to develop mucosal and systemic immune responses to each of the immunogens.

In another embodiment of the present invention, there is provided a mutant *C. fetus* strain in which all but one of the cassettes are replaced by a heterologous antigen. In this embodiment, one of the cassettes (e.g., sapA2) remains in its native configuration and the others are mutagenized. The advantage of this construction is that it also can induce immunity to *C. fetus* based on the single full-length SLP produced.

In another embodiment of the present invention, there is provided a mutant *C. fetus* strain in which recA is mutagenized. When the RecA protein is not produced, the DNA rearrangements permitting sapA antigenic variation can not occur at any detectable frequency. Thus, the *C. fetus* strain can only produce one of the SLPs encoded by one sapA homolog. This strain can be used, therefore, to colonize the host briefly, i.e. until protective immunity has developed to that homolog. Subsequently, the host immune response eliminates the organism. Thus, this mutant would provide effective immunity against subsequent C. fetus infection and is useful for vaccination of ungulates (including sheep, cattle and horses) in which infectious abortion and/or infertility can occur after the wild-type infection.

In another embodiment of the present invention, there is provided a C. fetus strain in which recA is mutagenized and the expressed sapA homolog is a chimera involving a heterologous peptide. In this embodiment, a mutagenized sapA homolog expresses a chimeric protein including a heterologous antigen. The strain is then passaged in vitro so that the chimeric homolog is in the expression position and then a recA mutation is made. This strain now essentially expresses only the chimeric protein thus providing a means to immunize a host to that antigen. The duration of colonization in the host is brief and this attenuated C. fetus strain allows safe immunization for the selected antigen.

In yet another embodiment of the present invention, there is provided a mixed mutant C. fetus strains each including a sapA chimera which is also a recA mutant. In this embodiment, mutants are constructed in which a single sapA homolog is mutagenized to encode a different chimeric protein representing a different heterologous antigen. Each mutant is also RecA-deficient due to mutation in recA. A host is inoculated with a mixture of two or more of these strains to provide immunization to the requisite antigens. Each strain is short-lived in the immunized host.

In another embodiment of the present invention there is provided a strain of E. coli carrying plasmids encoding the sapCDEF proteins that permits the secretion of chimeric proteins containing the SapA C-terminal secretion signal. The secreted protein is encoded by an altered sapA homolog that has been engineered so that the 5' section of the homolog-specific region is replaced by a DNA cassette encoding a heterologous antigen. Since the chimeric protein would be secreted by E. coli into the culture medium, this system provides a method for obtaining a large amount of the chimeric protein in a relatively pure form.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 2C shows the mapping of S-layer protein gene cassette arrangement by PCR. PCRs were performed with template chromosomal DNA from strains 23D and ACA2K mutants using sapA-specific 3' region forward (sapA) and km reverse (km) primers (left 4 lanes), sapA1-specific 3' region forward (sapA1) and km primers (middle 4 lanes), or sapA and sapA1-specific 3' region reverse (sapA1) primers (right 4 lanes). FIG. 2D shows the cumulative restriction maps of the 4 strains presented in FIGS. 2A–2C. The location of the probes as indicated from the hybridizations is shown under the map for each strain. sapAx represents an uncharacterized S-layer protein gene cassette; arrows represent direction of transcription; solid lines represent expressed genes, dashed lines represent silent genes; P over bent arrow represents the sapA promoter; the heavy line represents the 6.2 kb invertible promoter-containing element, flanked by opposing S-layer protein gene cassettes. The asterisks represent the palindromic putative recombinase recognition sites (TTAAGGAATCCTTAA (SEQ ID No. 12)) present in the 5' conserved region of each S-layer protein gene cassette (7), and restriction sites are indicated: H, HincII; N, NdeI; P, PstI.

Figure 2A:
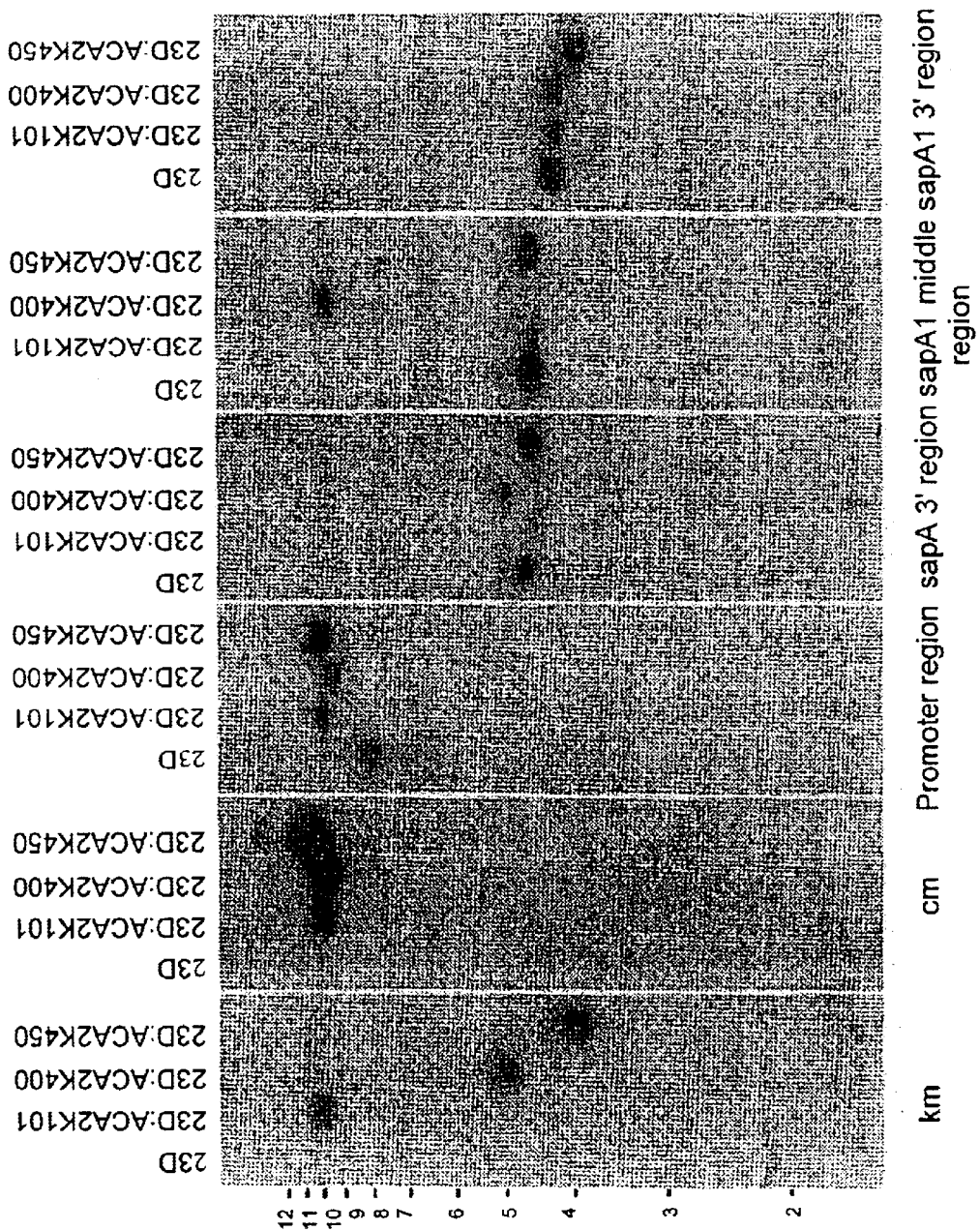
FIGS. 2A–D shows the Southern hybridization of HincII (FIG. 2A) or PstI (FIG. 2B) digestions of chromosomal DNA from C. fetus 23D and ACA2K series mutants using probes to km, cm, the promoter region, the sapA-specific 3' region, the sapA1-middle region, or the sapA1-specific 3' region. Each probe hybridized to a single fragment regardless of the phenotype of the C. fetus strain.
Figure 2B:
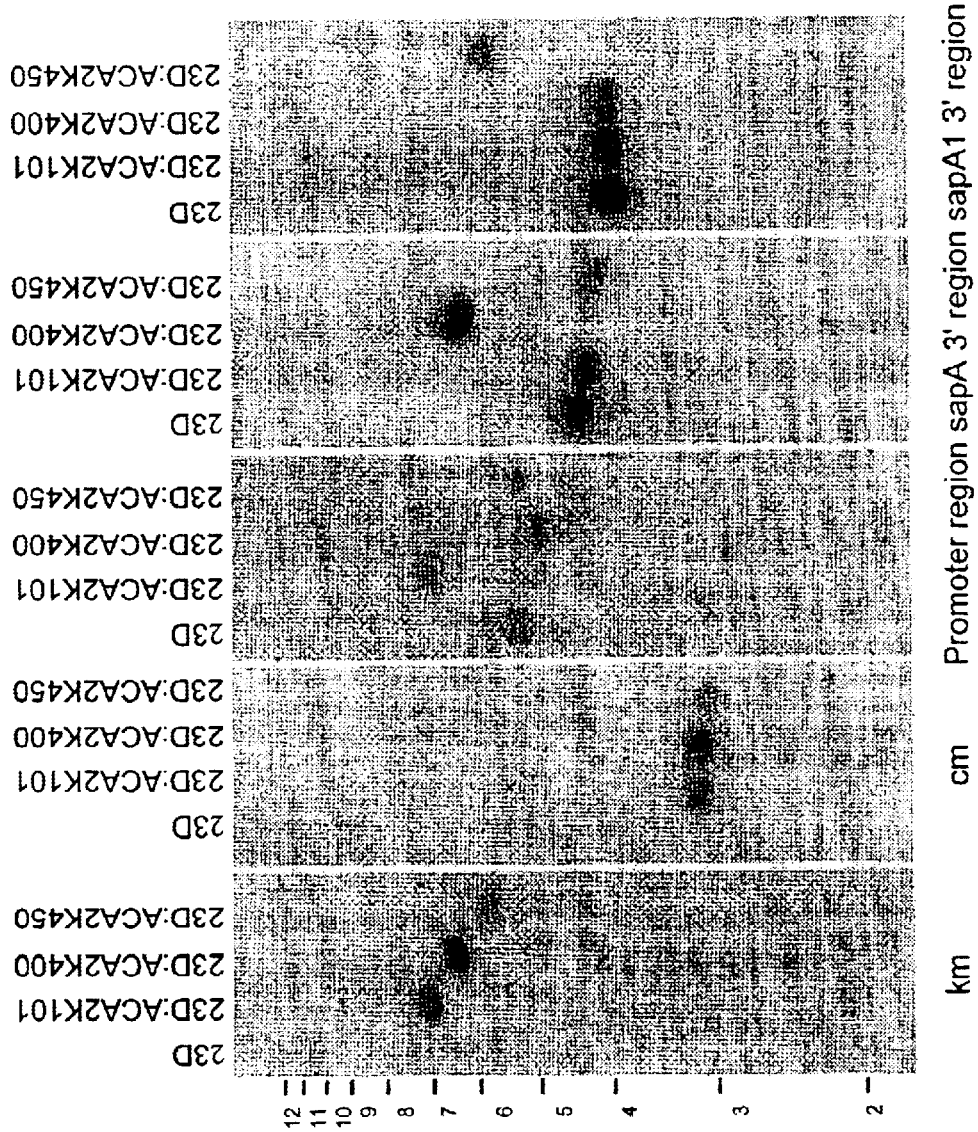
Figure 2C:
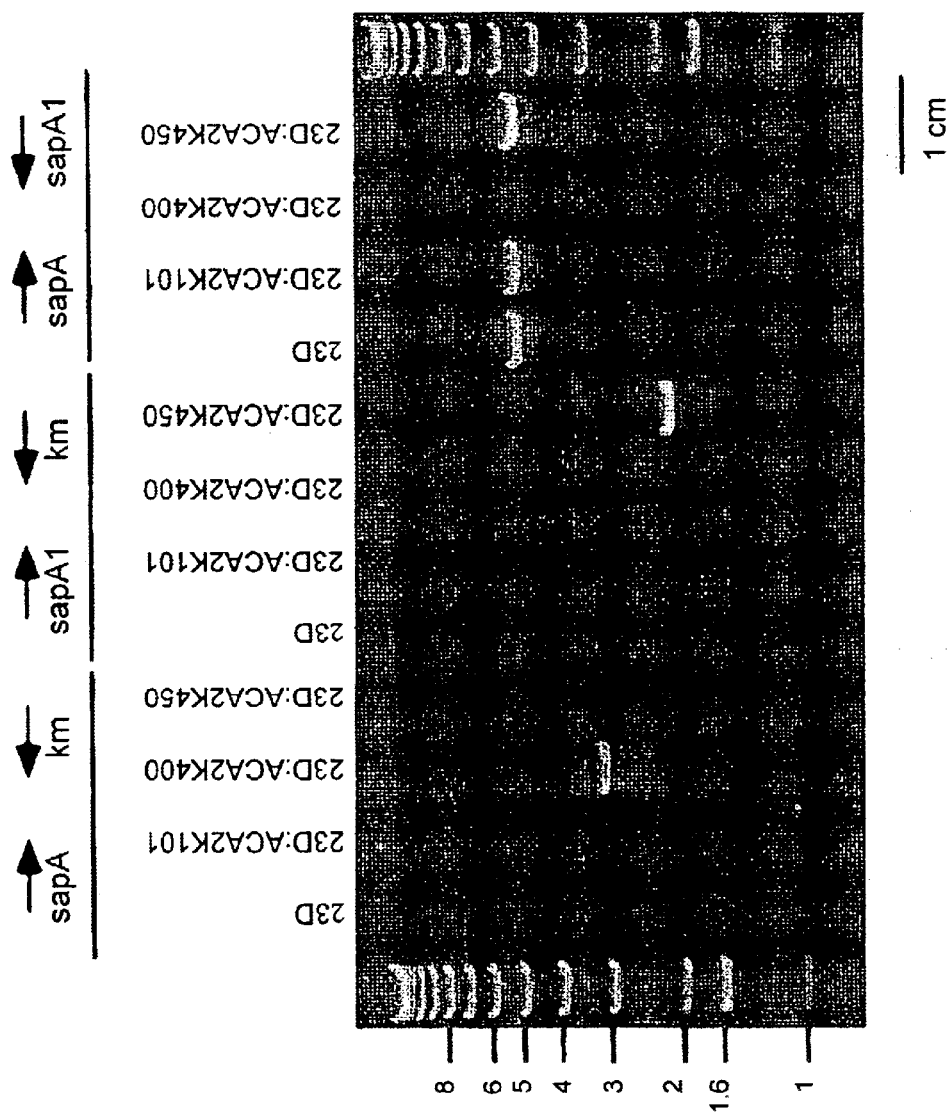
Figure 2D:
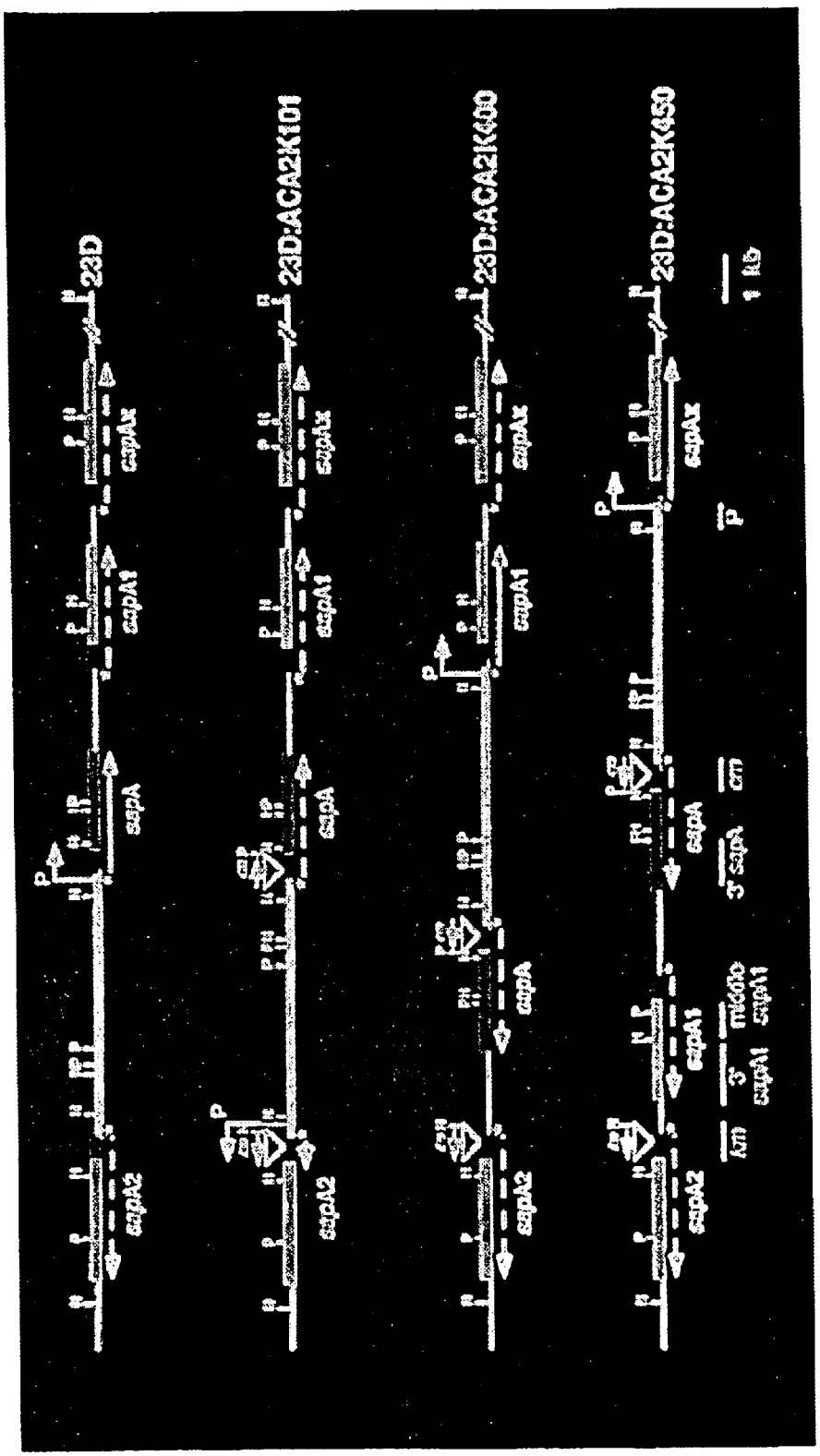

Inversion of DNA segments containing the promoter ('P' over bent arrow) permits expression of alternate S-layer protein gene cassettes (mRNA, arrow). Illustrated are inversion of the 6.2 kb promoter-containing element alone (left), the 6.2 kb element and one (middle) or two (right) S-layer protein gene cassette ORFs and the resultant genotypes. Each of these genotypes has been observed (FIG. 2D).

Figure 4:
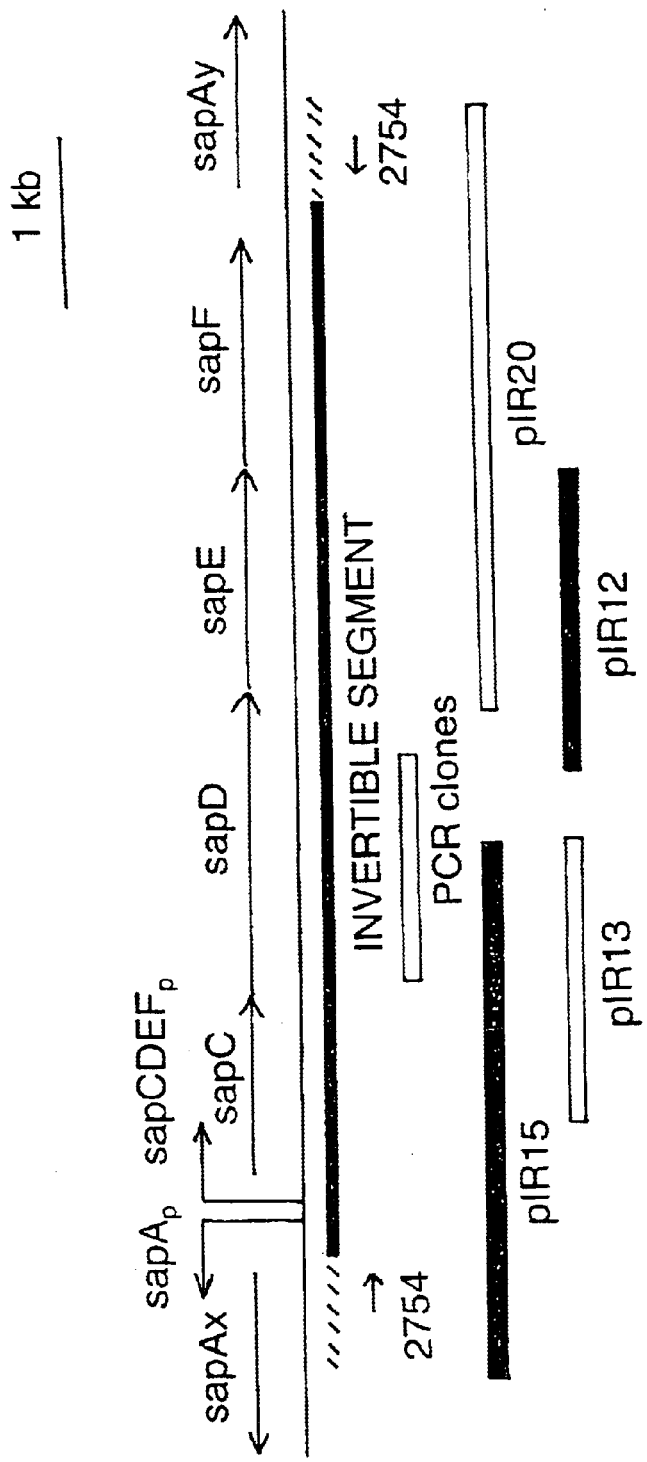

FIG. 4 shows a schematic representation of the sapA invertible region, showing the sapCDEF genes, the locations of the divergent sapA and putative sapCDEF promoters (bent arrows), and the clones (pIR15, pIR13, pIR12, and pIR20) from which the invertible region sequence was determined. The hatched areas represent the ca. 600 bp conserved regions at the 5' ends of sapA homologs flanking the invertible region (designated here as sapAx and sapAy), at which recombination occurs as the basis of sapA homolog rearrangements using S-layer protein antigenic variation.

Figure 5:
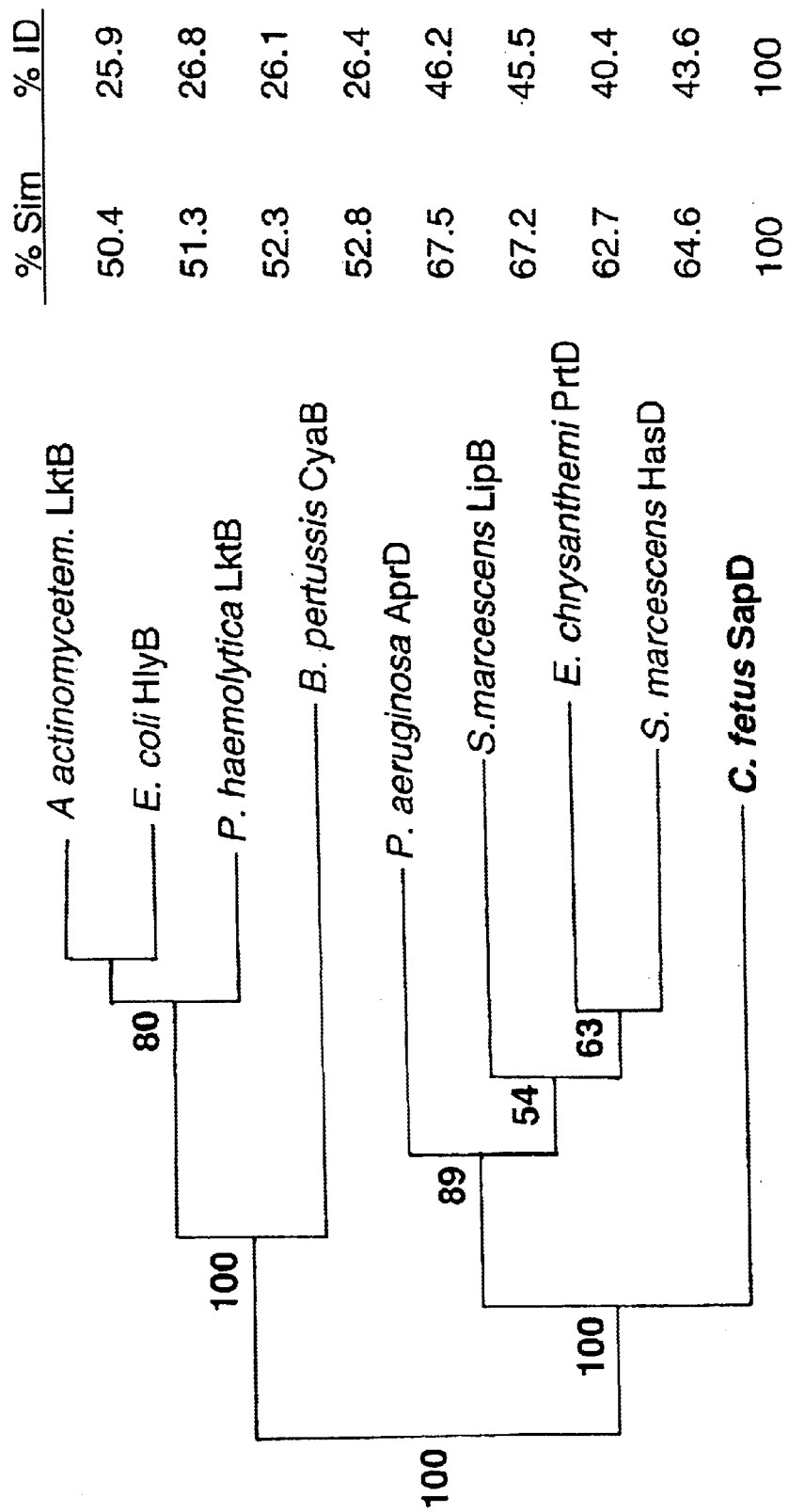

FIG. 5 shows a phylogram generated by parsimony analysis, demonstrating the relatedness of ABC transport proteins from type I secretion systems. The percent of amino acid similarity (% Sim) and identity (% ID) with *C. fetus* SapD is shown at the right. The bold numbers adjacent to the phylogram branches indicate the percentage of 1000 bootstrap replicates supporting the clustering of those branches. Branches without bootstrap values were clustered in less than 50% of bootstrap replicates.

Figure 6:
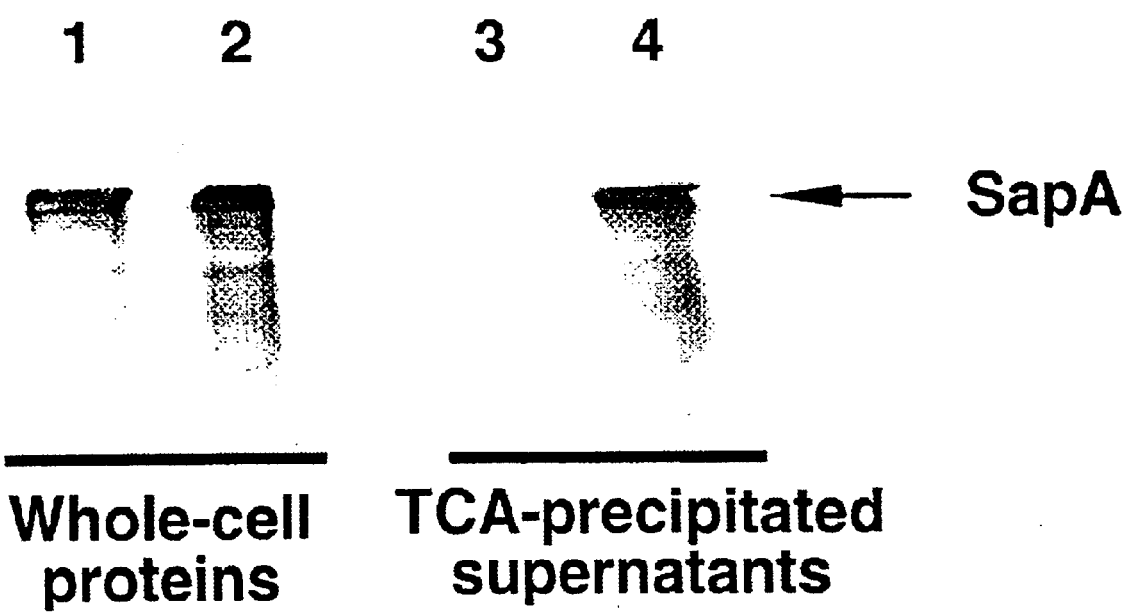

FIG. 6 shows an immunoblot detected with antiserum to SapA demonstrating the secretion of SapA from *E. coli* expressing *C. fetus* sapCEEF. One mg of whole cell proteins (lanes 1 and 2), or the amount of TCA-precipitate proteins present in 250 ml of culture supernatant (lanes 3 and 4) were analyzed. Lanes 1 and 3, C600 (pAMP1+pBCGYC1); and lanes 2 and 4, C600 (pIR100+pBCGYC1).

Figure 7:
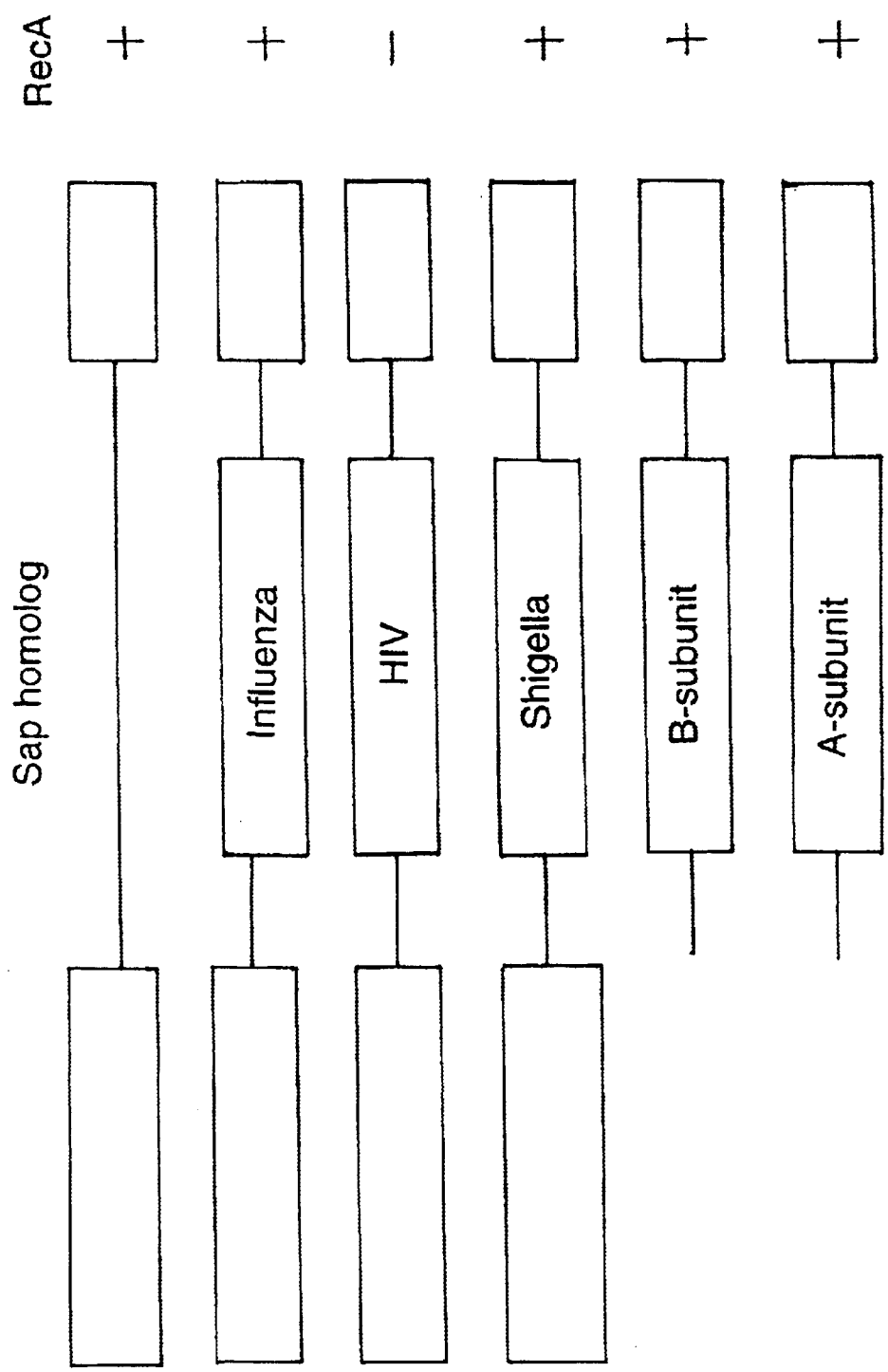

FIG. 7 shows several models of chimeric sap homologs for the use of *C. fetus* as a live vector for antigen delivery to the mucosal immune system. The left large gray box represents the N-terminal domain required for binding of the protein to the cell surface, the right sided smaller gray box represents the C-terminal domain required for secretion of the protein. The middle region shows the native sap homolog, and then in other examples, antigens related to influenza, HIV, Shigella, a model B-subunit of a toxin, or a model A subunit of a toxin. In the chimeras without the left sided gray box, the protein would be secreted without binding to the *C. fetus* cell surface. RecA at right refers to possible RecA status of the host *C. fetus* strain. If the strain is RecA$^-$ then it would only express a single cassette on its surface, but if RecA$^+$ (wild type), it would be able to switch the chimera it expressed.

DETAILED DESCRIPTION OF THE INVENTION

The following abbreviations may be used herein: S-layer protein, surface layer protein; km, kanamycin-resistance gene; cm, chloramphenicol-resistance gene; NHS, normal human serum.

In the present invention, programmed gene rearrangements are employed by a variety of microorganisms, including viruses, prokaryotes, and simple eukaryotes, to control gene expression. In most instances in which organisms mediate host evasion by large families of homologous gene cassettes, the mechanism of variation is not thought to involve DNA inversion. *Campylobacter fetus*, a pathogenic gram-negative bacterium, reassorts a single promoter, controlling S-layer (surface) protein expression, and one or more complete open reading frames strictly by DNA inversion. Rearrangements are independent of the distance between sites of inversion. These rearrangements permit variation in protein expression from the large S-layer protein gene family and suggest an expanding paradigm of programmed DNA rearrangements among microorganisms. Furthermore, S-layer proteins were secreted from *C. fetus* via a type I protein secretion system encoded by the sapCDEF operon. Secretory signal sequences for the SapA family of secreted proteins was localized to the carboxy-terminus of these proteins.

The present invention is directed to a mutant *C. fetus* strain useful for vaccinating an animal to *Campylobacter fetus*, wherein said strain is mutated to contain a DNA cassette encoding a heterologous protein. In one embodiment of the mutant *C. fetus* strain, a sapA homolog is altered. In one embodiment of the mutant *C. fetus* strain, the heterologous protein is a S-layer protein. Preferably, the encoded S-layer protein represents a chimera between the native S-layer protein and the peptide encoded by the cassette. Preferably, the cassette is selected from the group consisting of Salmonella, Shigella, *Campylobacter jejuni*, *E. coli* 0157:H7, human immunodeficiency virus (HIV), simian immunodeficiency virus (SIV) and other animal pathogens. In one embodiment of the mutant *C. fetus* strain, the cassette contains a 5' binding region and 3' secretion signal region and the protein is inserted between said binding region and said signal region. In another embodiment of the mutant *C. fetus* strain, the cassette contains a 3' secretion signal but has no binding region. Preferably, the protein is an antigen or a therapeutic agent.

The present invention is also directed to a method of immunizing a host to develop mucosal and systemic immune responses to an immunogen, comprising the step of administering to said host a pharmacologically effective dose of the strain described herein.

The present invention is also directed to a mutant *C. fetus* strain, wherein recA is mutated so that no functional RecA protein is produced, the DNA rearrangements permitting sapA antigenic variation occur at a very low frequency and wherein said *C. fetus* strain can only produce one of the S-layer proteins encoded by one sapA homolog. In one embodiment, this strain contains a sapA homolog expressing a chimeric protein including a heterologous antigen.

The present invention is also directed to a mixture of mutant *C. fetus* strains, wherein each strain includes a sapA chimera which is also a recA mutant, wherein a single sapA homolog is mutated to encode a different chimeric protein representing a different heterologous antigen and each mutant is also RecA-deficient due to mutation in recA. The present invention is also directed to a method of immunizing a host to develop mucosal and systemic immune responses to an immunogen, comprising the step of administering to said host a pharmacologically effective dose of these strains.

The present invention is also directed to a strain of bacteria modified to express SapCDEF genes Preferably, the strain is *Escherichia coli*. In one embodiment of this strain, a heterologous protein is expressed as a chimeric protein composed of sequences of heterologous origin, sequences that direct the secretion of said chimeric protein to the cell surface and sequences that direct the binding of the secreted chimeric protein to the lipopolysaccharides of the bacterial cell surface via the sapCDEF directed type I secretory system. The present invention is also directed to a method of immunizing a host to generate immune responses to an immunogen, comprising the step of administering to said host a pharmacologically effective dose of this strain.

The following examples are given for the purpose of illustrating various embodiments of the invention and are not meant to limit the present invention in any fashion.

EXAMPLE 1
Bacterial Strains and Culture Conditions

Wild-type S+ (possessing an S-layer) C. fetus strain 23D and spontaneous S− (no S-layer present) mutant strain 23B have been extensively characterized (4,5,12,13). Other C. fetus strains used were defined mutants derived from strain 23D, as described below. Stock cultures were stored and grown as described elsewhere (8). PVNT media containing 7 U/ml polymyxin B, 10 µg/ml vancomycin. 50 µg/ml naladixic acid. 10 µg/ml trimethoprim lactate, were supplemented for kanamycin-resistant strains or chloramphenicol-resistant strains, with 30 µg/ml kanamycin or 15 µg/ml chloramphenicol, respectively. E. coli strains used, including DH5α, HB101 and XLI-Blue (Stratagene, La Jolla, Calif.), were grown in L broth or on L plates (14).

Several bacterial strains have been deposited at ATCC with the following patent deposit designation: C. fetus strain 23D (PTA-4754), C. fetus recA mutant 97-211 (PTA-4753), E. coli DH5-α with plasmid pIR100 (PTA-4750), E. coli HB101 with plasmid pKO500 (PTA-4751), E. coli DH5-α with plasmid pKO505 (PTA-4752).

EXAMPLE 2
Chemicals and Enzymes

Isopropyl-β-D-thiogalactopyranoside (IPTG) (50 µg/ml) and 5-bromo-4-chloro-3-indolyl-β-galactoside (X-gal) (28 µg/ml) were purchased from Jersey Lab Supply (Livingston, N.J.). Restriction enzymes, T4 DNA ligase, Taq polymerase and E. coli DNA polymerase large (Klenow) fragment were from Promega and U.S. Biochemical Corp. (Cleveland, Ohio). Antibiotics were from Sigma Chemical Co. (St. Louis, Mo.), and [α-$^{32}$P]dATP (650 mCi/mmol) was from ICN Radiochemicals (Irvine, Calif.).

EXAMPLE 3
Genetic Techniques

Chromosomal DNA was prepared from 48 hour plate cultures, as described (9). Plasmids were isolated by the procedure of Birnboim and Doly (15). All other standard molecular genetic techniques were done, as described (14).

EXAMPLE 4
Construction of Mutant C. fetus Strains

Mutant C. fetus strains were created by mobilization of donor pKO500 or pKO505 plasmid constructs by conjugal mating as described elsewhere (9) with sequential selection (as shown in FIG. 1) on media containing 30 µg/ml kanamycin or 15 µg/ml chloramphenicol, or in the presence of 10% normal human serum (NHS), as described (16). pKO500: suicide hybrid plasmid with the sapA open reading frame disrupted with a chloramphenicol-resistance gene (cm) (17) located 127 base pairs into the open reading frame. pKO505: suicide hybrid plasmid with the sapA 2 open reading frame disrupted with a promoterless kanamycin-resistance gene (18) located 127 base pairs into the open reading frame.

EXAMPLE 5
Bactericidal Assays

To determine the susceptibilities of the mutant strains to the bactericidal activity of normal human serum, 10-fold serially-diluted cultures (starting from a single colony) were incubated at 37° C. for 60 minutes in the presence of 10% pooled normal human serum or 10% heat-inactivated normal human serum, as described (9, 16). Wild-type S+ strain 23D and spontaneous S− mutant strain 23B were the serum-resistant and serum-sensitive controls, respectively (9). Cultures then were plated to media containing chloramphenicol, kanamycin, or no antibiotic selection (FIG. 1A), and following incubation, bacterial colonies were enumerated. Survival rates were determined as the ratio of colony forming units (cfu)/ml in the presence of normal human serum or heat-inactivated human serum, or a similar ratio of cfu/ml in the presence or absence of the selective antibiotic.

EXAMPLE 6
Production of Antiserum to C. fetus S-Layer Proteins

Antiserum to the 97 kDa S-layer proteins of type A strain 82-40LP was raised in adult New Zealand White female rabbits and shows broad recognition of C. fetus S-layer proteins as described (5). To analyze wild-type and transconjugant C. fetus strains for S-layer proteins expression, cells were harvested from plates, lysed in sample loading buffer and examined by sodium dodecyl sulfate polyacrylamide gel electrophoresis (SDS-PAGE), and immunoblotting was performed as detailed (5,13).

EXAMPLE 7
Southern Hybridizations and Probes

C. fetus chromosomal DNA was digested with HincII and processed exactly as described (12). Probes included the gel-purified PCR products specific for the sapA promoter region (9), km, cm, 3' sapA region (1649 to 2760 bp), middle sapA1 region (620 to 1381 bp) and 3' sapA1-region (1381 to 2763 bp). Probes were $^{32}$P-radiolabeled by primer extension with random hexameric oligonucleotides (19). Polymerase chain reactions were performed as described (9).

EXAMPLE 8
Polymerase Chain Reaction

Polymerase chain reactions were performed as described (9). Amplification of large PCR products was accomplished by denaturing for only 5 seconds and extending at 68° C. for longer periods, typically 4–7 minutes. Primers used include:

km F, 5'-TGTAGAAAAGAGGAAGGAAA-3'(SEQ ID No: 1);

km R; 5'-CTAAA ACAATTCATCCAGTA-3'(SEQ ID No: 2);

cm F, 5'-AGTGGATAGATTTATGATATAGTG-3'(SEQ ID No: 3);

cm R, 5'-T TTATTTATTCAGCAAGTCTTG-3'(SEQ ID No: 4);

sapA F middle, 5'-CATCTCTACAGCAGCAAAAG-3' (SEQ ID No: 5);

sapA F 5'-GCGGAGATAATGTTGTAGTTGAT G-3' (SEQ ID No: 6);

sapA R, 5'-AACTTTAAGAT CTAGCGTACC-3'(SEQ ID No: 7);

sapA1 F middle, 5'-AGGGTACTGATTTAGACGATA-3' (SEQ ID No: 8);

sapA1 F 3',5'-GCTGGATTTACAGGAGATTTAACC-3' (SEQ ID No: 9);

sapA1 R 3' #1,5'-GTTACTGGTATCAATAA CAACATAAGT-3' (SEQ ID No: 10);

sapA1 R 3' #2,5'-CTACGTAATCATACTGCTACC-3' (SEQ ID No: 11).

EXAMPLE 9
Construction and Phenotypic Analysis of Mutant Strains

Figure 1A:
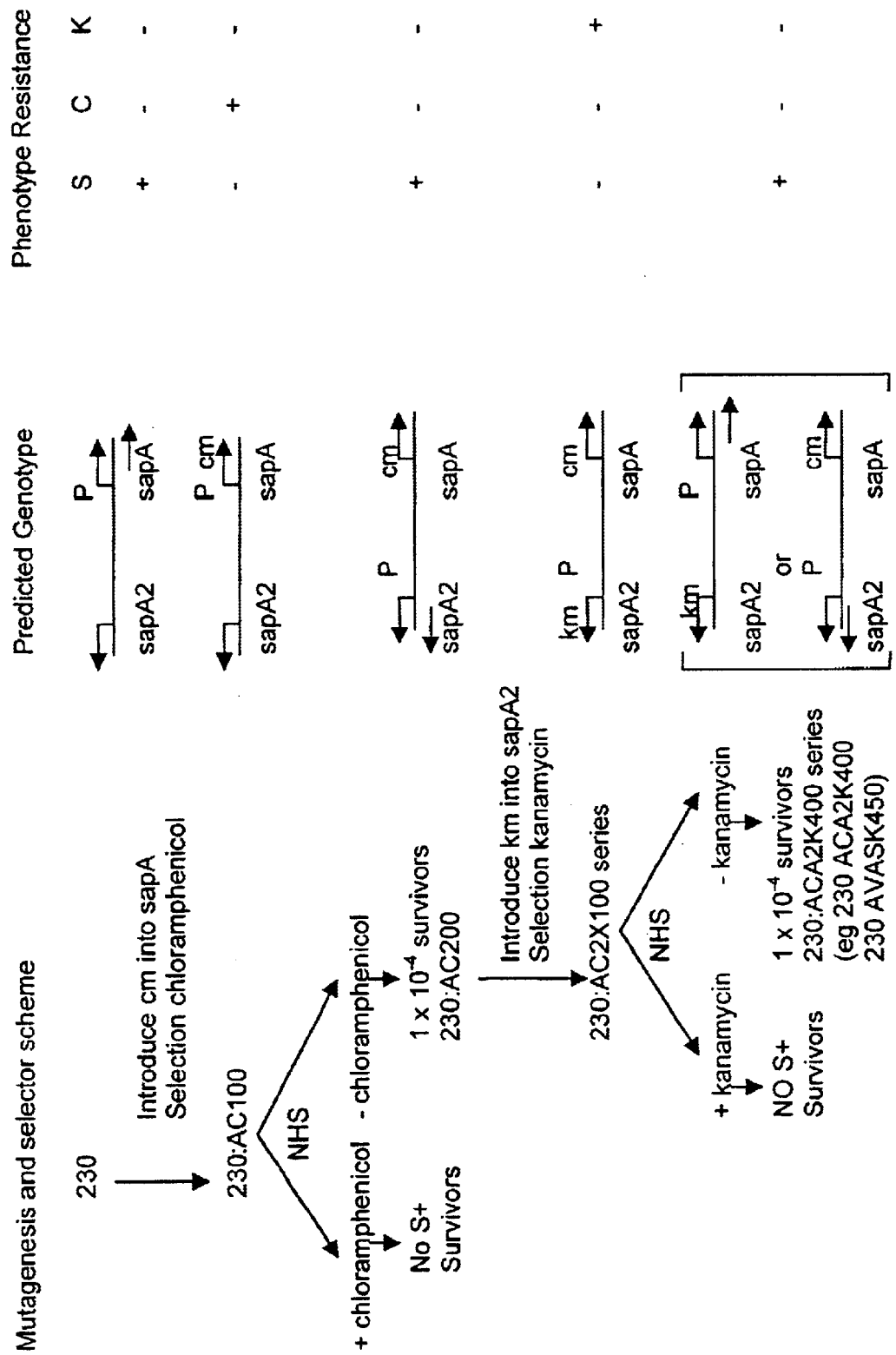
FIGS. 1A&B shows the schematic representation of serial experiments to utilize km- and cm-cassettes to examine S-layer proteins gene rearrangement (FIG. 1A). Introduction of cm into strain 23D by marker rescue led to insertion into sapA to create 23D:AC100. This strain was selected on chloramphenicol-containing medium, and as expected was chloramphenicol (C) resistant, and was S$^-$ (no S layer) and not resistant to serum (S) and kanamycin (K), as previously reported (9). Incubation of 23D:AC100 with normal human serum (NHS) selected for survivors (at a frequency of $1\times10^{-4}$ (AC200 series) that were S$^+$ (S-layer present) and serum-resistant but sensitive to kanamycin and chloramphenicol. Strain 23D:AC200, expressing sapA2, was further mutagenized by introduction of km into sapA2 to create the 23D:ACA2K100 series. These strains were S$^-$ and serum- and chloramphenicol-sensitive but kanamycin-resistant. Incubation with NHS selected for survivors (at a frequency of $1\times10^{-4}$) that were S$^+$ and serum-resistant but kanamycin- and chloramphenicol-sensitive (ACA2K400 series). The reciprocal relationship between antibiotic and serum-resistance suggests that only a single promoter for S-layer protein gene cassettes is present. All ACA2K400 series strains must have an S-layer protein gene cassette other than sapA or sapA2 positioned downstream of the single S-layer protein promoter. The predicted genotypes are depicted. P, sapA promoter; bent arrow, location and direction of transcription of S-layer protein gene cassette; solid inverted triangles, antibiotic resistance gene insertion; NHS, normal human serum.
Figure 1B:
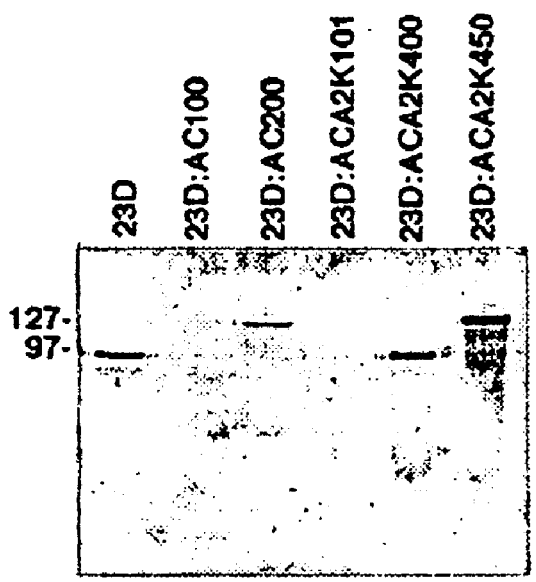
FIG. 1B shows the immunoblot of C. fetus strain 23D and selected mutants into which cm or cm and km were inserted into S-layer protein gene cassettes. As expected, all the serum-resistant strains expressed S-layer proteins (of 97 or 127 kDa) recognized by antiserum to conserved C. fetus S-layer proteins determinants whereas there was no expression for strains maintained on either antibiotic.

To show that both the sapA promoter and the complete structural genes can be mobilized by DNA inversion, mutant strains were created in which both S-layer protein-encoding gene cassettes bracketing the invertible sapA promoter were disrupted (FIG. 1A). First, insertion of a chloramphenicol-resistance cassette (cm) into the open reading frame (ORF) of the expressed S-layer gene cassette (SapA) ablated SapA expression (FIG. 1B) and rendered the organism (23D:AC100) serum-sensitive. Using the ability of S+ (but not S−) C. fetus strains to survive incubation in normal human serum (4, 13, 20–22), mutants (9) expressing the sapA2 cassette were then selected for promoter inversion and identified strain 23D:AC200 (FIG. 1). Next, 23D:AC200 was mutagenized by insertion of the kanamycin-resistance cassette (km) to ablate SapA2 expression, creating 23D:ACA2K101 (FIGS. 1 and 2D). Incubation of this dually disrupted strain in serum selected for serum-resistant survivors. These were found at a frequency of $1\times10^{-4}$, and as expected, expressed S-layer proteins of 97 kDa or 127 kDa (FIG. 1B) and were antibiotic-sensitive. Immunoblot of 26 serum survivors demonstrated that 16 (62%) expressed a 97 kDa (e.g., 23D:ACA2K400) and 10 (38%) expressed a 127 kDa (e.g., 23D:ACA2K450) S-layer proteins. These results suggested that in each of the survivors there had been exchange of at least one of the bracketing cassettes. None of the mutant strains maintained on antibiotic-containing media produced an S-layer proteins band, as revealed by immunoblot, (FIG. 1*b*), and this shows that expression of cm or km is dependent on the single sapA promoter. These experiments provided a group of well-defined strains with which to examine the genotypic events associated with the observed phenotypic variations.

EXAMPLE 10

Phenotypic Variation is Associated with Nested DNA Inversions

To investigate the nature of the recombination event that allowed the single sapA promoter to express a native S-layer gene cassette in the dually disrupted strains, using Southern analyses, these organisms were compared with wild-type *C. fetus* strain 23D and the $S^-$ parental mutant 23D:ACA2K101. The known positions of HincII (FIG. 2A), PstI (FIG. 2B), and NdeI (data not shown) sites located in sapA, sapA1 and sapA2 (8,9,23,24) were used to predict the size of the fragments hybridizing with appropriate probes. The promoter region, the sapA-3' region, the sapA1 middle region and the sapA1–3' region probes hybridized to 8.5 kb, 4.8 kb, 4.8 kb and 4.3 kb HincII fragments, respectively, in wild-type strain 23D (FIG. 2A). Based on these and previous Southern hybridization and PCR data (9), the location of these genes relative to one another in wild-type strain 23D was defined (FIG. 2D, top line).

An identical hybridization pattern was observed for mutant 23D:ACA2K101 with the exception that the km and cm probes hybridized to a 10.4 kb fragment and that the promoter region probe also hybridized to a 10.4 kb fragment, (FIG. 2D, line two). These results are entirely consistent with the introduction of the km (0.8 kb) and cm (1.1 kb) markers flanking the promoter. For the mutant strains ACA2K400 and ACA2K450, changes in phenotype were clearly associated with change in probe co-hybridization (FIG. 2A). In mutant strain 23D:ACA2K400, the km probe hybridized to the same 5.1 kb fragment as the sapA-3' region probe and in strain 23D:ACA2K450 to the same 4.0 kb fragment as the sapA1–3' region probe (FIG. 2A), whereas the promoter region probe hybridized to fragments larger than 9 kb. For each of the mutant strains, the cm and promoter region probes hybridized to fragments of identical sizes (FIG. 2A). These results demonstrate that the open reading frames had inverted (FIG. 2D), and reflect the differing locations of each of the S-layer protein gene cassettes in relation to the km marker. The total size of non-overlapping hybridizing fragments remained constant among the strains (17.6 kb in wild-type and, reflecting addition of the two antibiotic resistance cassettes, 19.5 kb in all mutant strains) indicating that recombination did not involve net duplication or deletion of DNA (FIG. 2*d*).

Following PstI digestion, as expected, the km probe hybridized to the same 7.3 kb, 6.5 kb, and 5.9 kb fragments as the promoter region probe, the sapA-3' region probe and the sapA 1–3' region probe in strains ACA2K101, ACA2K400 and ACA2K450, respectively (FIG. 2B). Despite the genotypic differences among the mutant strains, the constancy of the 3.1 kb fragment hybridizing with the cm probe (FIG. 2B) was consistent with the position of the marker downstream of the promoterless end of the 6.2 kb invertible element (FIG. 2D). Hybridization of the promoter region probe to 5.5 kb, 4.9 kb and 5.3 kb fragments in strain 23D and mutants ACA2K400 and ACA2K450, respectively, also reaffirms the model. The sapA-3' region probe hybridized with a 4.1 kb fragment in strains 23D, and mutants ACA2K101 and ACA2K450, but not ACA2K400 (FIG. 2B), consistent with the locations of PstI sites within sapA and sapA1, and the tandem relationship between these two cassettes. Similarly, the sapA 1–3' region probe hybridized with a 4.2 kb fragment in strains 23D, ACA2K101 and ACA2K400, but not ACA2K450 (FIG. 2B), consistent with the tandem relationship between sapA1 and the downstream sapAx in the first three strains. The observed sizes of each of the hybridizing fragments and their co-hybridization patterns in PstI (FIG. 2B) or NdeI-digested (not shown) genomic DNA using similar probes were completely consistent with the known restriction sites (8,9,23,24) as depicted in FIG. 2D.

PCR analyses provided independent confirmation for open reading frame inversion. The 3' sapA-specific forward primer and a km reverse primer yielded a product for strain 23D:ACA2K400 (FIG. 2C), indicating that sapA had inverted and was located immediately upstream of km. Similarly, for strain 23D:ACA2K450 the data (FIG. 2C) indicate that sapA1 had inverted and was located immediately upstream of km. PCR analyses using the 3' sapA-specific forward primer and 3' sapA 1specific reverse primer yielded a 4.3 kb product for all strains except for 23D:ACA2K400 (FIG. 2C, rightmost 4 lanes), indicating that the tandem relationship of sapA and sapA1 was lost in strain ACA2K400. The data indicate that for mutant strains 23D:ACA2K400 and 23D:ACA2K450, sapA, or both sapA and sapA1, respectively, have inverted in relationship to sapA2 (FIG. 2D, lines 2–4).

EXAMPLE 11

DNA Inversion Events Occur Independent of the Distance Between Recombination Sites The frequency of the DNA inversion events was determined, involving promoter alone, or promoter and one or more of the gene cassettes. The mutant strains (TABLE 1) provided easily definable phenotypes with which to assess the inversion events. These were measured by conducting experiments in which the strains were examined for resistance to a selection that would be lethal (exposure to kanamycin, chloramphenicol, or serum) unless defined inversions allowing expression of genes to overcome the exposure had occurred. Events involving inversion of the promoter-containing element alone, or together with one or two open reading frames, occurred at nearly equal frequency (~1 to 2.6×10$^{-4}$) (TABLE 1). These data imply that inversions involving two adjacent open reading frames occurred in a single event and did not result from two or more sequential inversion events. Recombination occurs at either homologous or palindromic DNA sequences (9). The distance-independence between sites suggests that inversion occurs by a random collision model, as proposed (25).

homologs, and may play a role in the inversion of this DNA segment. As a potential component of this recombination mechanism, sequences resembling χ sites (RecBCD recognition) were present at positions 31–38 and 6192–6199. Several potential σ$^{70}$-like promoters were noted 44–243 bp upstream of sapC. These putative sapCDEF promoters were oriented in the opposite direction to the

TABLE 1

C. fetus survival after serum or antibiotic selection

| | Relevant Phenotype | | | Immunoblot | | | | |
|---|---|---|---|---|---|---|---|---|
| | Susceptibility | | | presence of | | No. of | Survival. × 10$^{-4}$ | |
| Strain | to Chlor. | Kana. | Serum | S layer: kDa | Selection* | Exper. | Mean | Range |
| 23D:AC100 | R | S | S | — | Serum | 7 | 1.0 | 0.2–3.1 |
| 23D:AC200 | S | S | R | 127 | Chloram. | 6 | 1.2 | 0.1–2.5 |
| 23D:ACA2K101 | S | R | S | — | Chloram. | 12 | 0.7 | 0.2–2.5 |
| 23D:ACA2K101 | S | R | S | — | Serum | 8 | 1.2 | 0.2–1.4 |
| 23D:ACA2K200 | R | S | S | — | Kanamycin | 3 | 0.8 | 0.4–1.1 |
| 23D:ACA2K400 | S | S | R | 97 | Kanamycin | 6 | 1.0 | 0.8–1.4 |
| 23D:ACA2K400 | S | S | R | 97 | Chloram. | 6 | 1.2 | 0.6–2.2 |
| 23D:ACA2K450 | S | S | R | 127 | Kanamycin | 5 | 2.6 | 1.2–4.6 |
| 23D:ACA2K450 | S | S | R | 127 | Chloram. | 6 | 2.5 | 1.0–4.6 |

S: sensitive;
R: resistant;
Chloram.: chloramphenicol.
*Selection by plating cells to media supplemented with 15 μg/ml chloramphenicol or 30 μg/ml kanamycin, or incubating cells in 10% NHS for 60 min at 37° C..

EXAMPLE 12
Cloning of the Invertible Region

Since bacterial genes involved in similar functions are often clustered, the 6.2 kb invertible region between two sapA homologs was characterized. The 6.2 kb fragment was first amplified by PCR, and this product was subcloned into pAMP1 to yield the plasmid pIR100. Next, this subcloned fragment was used as a probe to isolate a series of overlapping plasmid clones derived from a C. fetus 23D genomic library constructed in λZAPII. Four of these, designated pIR15, pIR13, pIR12, and pIR20 represented the majority of the invertible region and were subjected to DNA sequence analysis. In order to determine the sequence of the small sequence gap between pIR13 and pIR12, a DNA segment was amplified from C. fetus 23D genomic DNA by PCR using appropriate primers and subcloned into pT7Blue. To avoid the problem of PCR-induced errors, three independent subclones were sequenced and in each case the sequence was identical.

EXAMPLE 13
Analysis of Invertible Region Features

The DNA sequence of the 6229 bp invertible region from strain 23D was predicted to contain four open reading frames, which were designated sapCDEF (FIG. 4). The sapC gene began 596 bp from the initiation codon of the oppositely-oriented upstream sapA homolog. The sapC open reading frame was 1035 bp in length and was immediately followed by the sapD, sapE, and sapF open reading frames, which were 1752, 1284, and 1302 bp, respectively. Each gene in this cluster had a typical ribosome binding site, and overlapped the preceding gene, by 14 bp (sapC/D), 1 bp (sapD/E), and 11 bp (sapE/F). The sapF gene ended 287 bp upstream of the sapA homolog located downstream. The 74 bp preceding the ATG codons initiating translation of the sapA homologs flanking sapCDEF were identical to each other (FIG. 4). These conserved segments have previously been noted upstream of the three characterized sapA sapA promoter, with the two −35 regions separated by 200–380 bp. Due to the overlapping nature of the sapCDEF genes and the lack of other putative promoters, it is likely that they are co-transcribed.

EXAMPLE 14
Similarities of SapCDEF to Other Proteins

The sapC open reading frame predicted a protein product of 344 amino acids (39.7 kDa) that had no significant similarities in the non-redundant database maintained by NCBI. In contrast, the products of the sapDEF genes had high similarity to proteins encoding type I secretion systems. SapD (584 amino acids, 64.0 kDa) was related to the ABC family of transporters, especially those that are involved in the translocation by type I secretion systems of proteases, lipases, hemolysins, and leukotoxins across the envelopes of gram-negative bacterial pathogens. The degree of similarity between SapD and these proteins was between 68% similarity (with *Pseudomonas aeruginosa* AprD) and 50% similarity (*Actinobacillus actinomycetemcomitans* LktB). In addition, SapD contained two motifs found in such proteins, an ATP/GTP binding site (GPSAAGKS (SEQ ID No. 13); Walker Box A, amino acid residues 365–377) and a peptide (LSGGQRQRVALA (SEQ ID No. 14); amino acid residues 468–479) that is a signature sequence for ABC transporters. The SapE protein (428 aa, 47.9 kDa) was similar to the MFP proteins of type I transporters, typified by *P. aeruginosa* AprE (52% similar) and *E. coli* HlyD (49% similar). SapF (434 amino acids, 49.4 kDa) was related to the outer membrane component of type I systems, such as *P. aeruginosa* AprF (45% similar), *Erwinia chrysanthemi* PrtE (41% similar), and *E. coli* TolC (47% similar). Parsimony and bootstrap analyses supported the classification of the *C. fetus* transport proteins on phylogenetic branches distinct from other type I secretion apparatuses (FIG. 5).

EXAMPLE 15

Construction of a sapD Mutant

To examine whether genes in the C. fetus invertible region encoded proteins responsible for SLP secretion, a derivative of type A strain 23D containing an insertional mutation in sapD was constructed. To generate a sapD mutation, an aphA cassette was inserted into a unique BglII site within sapD and transformants were selected on plates containing kanamycin. This new clone was designated pIR131. The sapD insert containing the resistance fragment was subcloned into suicide vector pILL570 to yield pILL131, which was transformed into E. coli S17-1. Transformants were selected from trimethoprim/kanamycin plates and verification of pILL131 was made by digestion with HindIII. The mob+ E. coli strain S17-1 containing IncP DNA transfer functions and pILL131 was used as the conjugation donor, and C. fetus wild-type strain 23D was the recipient. Approximately five thousand transconjugants were recovered (frequency of $4 \times 10^{-6}$ transconjugants per recipient). Chromosomal DNA from one of these strains was extracted and digested with NdeI for Southern analysis, using hybridization probes for sapD, aphA, and pILL570. The sapD probe hybridized with a 4.2 kb NdeI fragment in wild-type strain 23D, exactly as predicted from the DNA sequence of the invertible region. The size of the NdeI fragment in strain 97-205 hybridizing to the sapD probe was 5.6 kb indicating the incorporation of the 1.4 kb aphA cassette in sapD, as expected. The hybridization of the aphA probe with a fragment of 5.6 kb in 97-205 but not in 23D was consistent with this observation. A pILL570 probe did not hybridize with DNA from 97-205, indicating that 97-205 was derived from a double crossover event in which only the mutagenized sapD allele was incorporated into the chromosome. PCR experiments using sapD- and aphA-specific primers confirmed the Southern hybridization data. These results indicate that a strain containing an insertional mutation in sapD has been successfully constructed.

EXAMPLE 16

Properties of a C. fetus sapD Mutant

Whether the C. fetus sapD mutant strain 97-205 was able to export S-layer proteins and to assemble a functional S-layer on its surface was next determined. First, the ability of the wild-type and sapD mutant strain to resist complement-mediated killing, a phenotype consistent with the presence of the S-layer was examined. Suspensions of cells were exposed either to normal human serum or to heated-inactivated normal human serum, and the extent of complement-mediated killing was determined. As expected, the S+strain 23D was completely resistant to killing (0.31 $\log_{10}$ kill). In contrast, as expected, there was approximately three $\log_{10}$ killing of strain 23B (3.34 $\log_{10}$ kill), that is unable to express an S-layer. Results for strain 97-205, the sapD mutant (3.04 $\log_{10}$ kill), were nearly identical to that for 23B, and are consistent with the absence of a functional S-layer on the surface of sapD mutant strain 97-205.

To understand the basis for the scrum-susceptibility of the sapD mutant, immunoblots were performed to detect the presence of SLPs on the cell surface. S-layer proteins can readily be removed from the surface of S+ cells by washes with distilled water. Therefore, water washes and whole-cell proteins of wild-type and sapD mutant cells were analyzed by immunoblot with polyclonal antiserum against SLPs. In the wild-type strain, S-layer proteins were detected both in whole-cell samples and water washes, as expected for cells expressing a functional S-layer, whereas no S-layer proteins were detected for S⁻ strain 23B. In the sapD mutant, however, S-layer proteins were not detected either extracellularly or in whole-cell samples. Thus, disruption of sapD by the insertion of an antibiotic-resistance cassette had the effect of eliminating S-layer proteins expression altogether, as well as their secretion. Primer extension analysis indicated approximately wild-type levels of sapA mRNA in the sapD mutant 97-205, indicating that the effect of the sapD mutation on the inability to detect SLPs in the cytoplasm was not due to a regulatory effect on S-layer protein gene transcription.

EXAMPLE 17

Secretion of SapA from E. coli Expressing sapCDEF

To determine whether sapCDEF permits the secretion of SapA, the ability of E. coli strains carrying pIR100 to mediate the specific secretion of C. fetus SapA was tested. E. coli C600 cells were isolated that had been transformed with pBGYC1, a pACYC184-derived plasmid containing C. fetus sapA, and either pIR100 (sapCDEF) or pAMP1 alone (vector control). SapA secretion was assayed using immunoblots to indicate the appearance of SapA in filtered, trichloroacetic acid (TCA)-precipitated culture supernatants prepared from these strains. As expected, both E. coli strains produced SapA (FIG. 6). Secretion of SapA was detected only in supernatants from E. coli cells expressing sapCDEF (FIG. 6). These results indicate that the C. fetus sapCDEF genes were sufficient to allow E. coli to secrete SapA.

EXAMPLE 18

Conserved Features of S-Layer Protein C-Termini

Proteins that are transported by type I secretion systems do not have the N-terminal signal peptides that are conserved in proteins exported by type II systems. Type I secretory proteins rely upon signals that are located at their extreme C-termini. However, these signals tend to have little primary sequence homology, and their exact structures have been difficult to elucidate. In an attempt to define candidate sequences/structures for C-terminal secretion signals in bacterial SLPs, the C-terminal 70 amino acids of four C. fetus SLPs for which the sequences are known (SapA, SapA1, SapA2, and SapB) were aligned.

Several conserved peptides were evident. The sequence GDGS(T/G) (SEQ ID No. 15) was present in three of the four S-layer proteins, with SapA2 possessing a slightly different version SKGST (SEQ ID No. 16). Similarly, the peptide GxTYVV(V/I)D (SEQ ID No. 17) was present in three of the four SLPs with the corresponding sequence (GxTYVVda (SEQ ID No. 18)) again being slightly more divergent. Several other conserved amino acid residues also were apparent. The DVIV (SEQ ID No. 19) motifs implicated in protease secretion were not present per se at the extreme C-terminus of any of the S-layer proteins, although similar sequences (DGSVI (SEQ ID No. 20)) were found at the C-termini of the SapA and SapB proteins. Similar to type I-secreted toxins and related exoproteins, the S-layer proteins had 1–4 hydroxylated residues (S or T) within the C-terminal ten amino acids.

To investigate whether the C-terminal domains of these S-layer proteins also could form similar secondary structures, each of these peptides was analyzed using the programs of Garnier et al. The predicted C-terminal secondary structures (α-helix, β-sheet, amphipathic peptides, and turn-forming residues) were then superimposed on the alignment of the 4 C-terminal peptides. Three of these peptides (SapA, SapA1, and SapB) consisted of segments predicted to form sheet-sheet-helix-sheet, with each of these domains separated by turn-forming. The C-terminal domain of SapA2 was predicted to form a structure of helix-sheet-helix-sheet. Furthermore, the sheet-forming regions of all 4 proteins, as well as the most N-terminal helix-forming region of SapA2, were predicted to be amphipathic. Taken together, these results suggest that the C-termini of four *C. fetus* S-layer proteins contain conserved sequences and secondary structures that are candidates for secretion signals.

S-layer proteins expression in *C. fetus* is based on the single sapA promoter present on an invertible 6.2 kb element, that is bracketed by inverted repeats and oppositely oriented cassettes, sapA and sapA2, that are subject to substitution (9). By creation of appropriate mutants and by using selection for phenotypic properties, the present invention demonstrates that DNA rearrangement can involve inversion of this element in concert with one or more of the tandemly arrayed S-layer protein gene cassettes.

Figure 3:
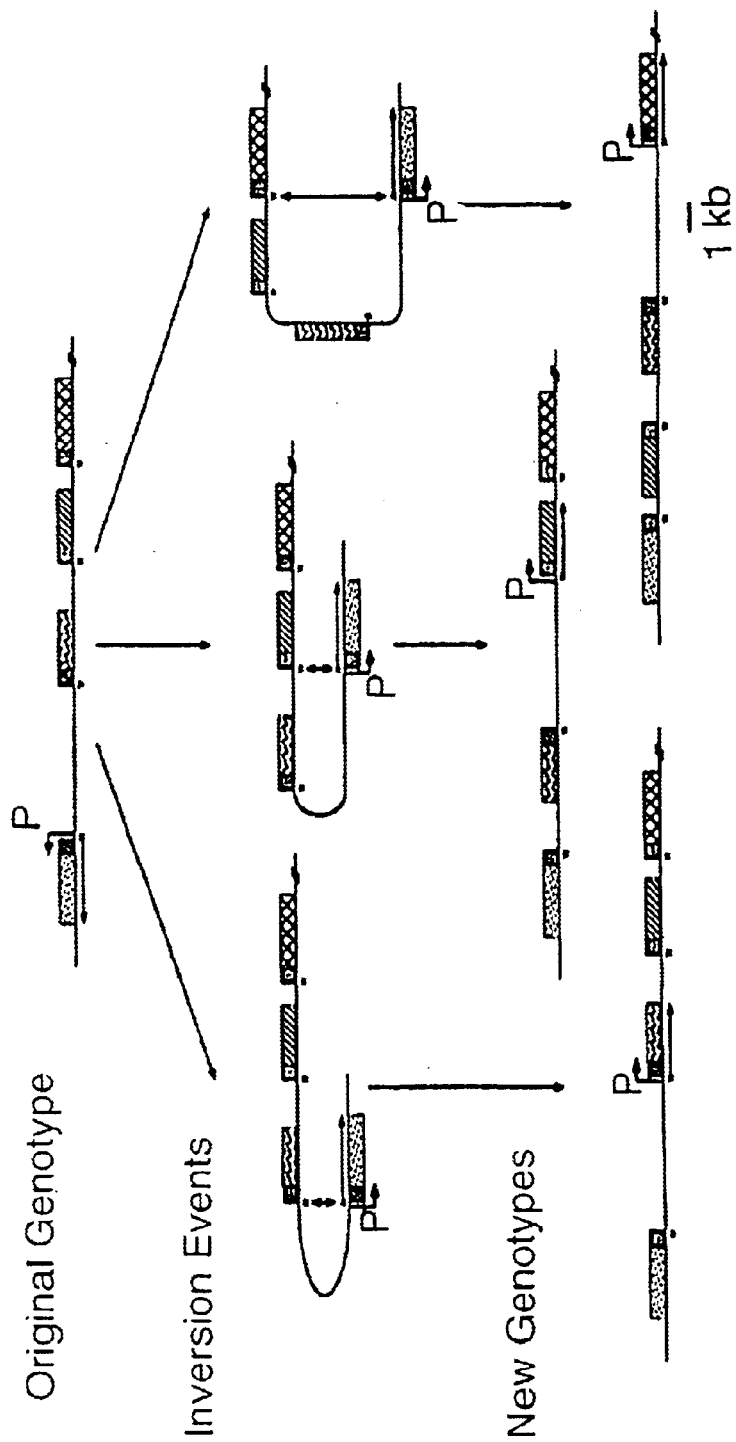
FIG. 3 shows the proposed model of molecular events involved in S-layer protein gene cassette rearrangement by DNA inversion. DNA inversion between two oppositely oriented cassettes follows DNA strand exchange at the putative recombinase target site (asterisk) found upstream of each S-layer protein gene cassette within the 5' conserved region (small grey box) (8). Patterned boxes represent variable regions of S-layer proteins gene cassettes. A 6.2 kb intervening segment is topologically reversed leading to ordered rearrangement of the S-layer protein gene cassettes.

DNA inversion has been believed to involve mutually exclusive promoter or structural gene inversion. Either the promoter inverts relative to fixed structural genes (26,27), or structural genes invert downstream of a fixed promoter (28-30) permitting expression of two alternate gene copies (10,11). The system of DNA inversion in *C. fetus* is novel because it combines the features of each mechanism as both the promoter and the structural genes are mobile, which permits the shuffling of complete genes and their ultimate expression (FIG. 3). Rearrangement of the S-layer protein gene cassettes permits the organism to vary S-layer protein expression and surface antigenicity allowing for evasion of host immune responses. This inversion system differs from the *Mycoplasma pulmonis* vsa gene inversion, which rearranges only incomplete coding regions and demonstrates less sequence stability.

The present invention further indicates that inversion occurs randomly between open reading frames of opposite orientation independent of the size of the intervening DNA segment. The economy of a simple inversion system may be especially useful for *C. fetus* which has a relatively small (1.1 megabase) genome (32); the strict conservation of both coding and non-coding regions related to the sap homologs in type A and type B strains (7) is consistent with the importance of this efficient system. The present invention expands the paradigms of DNA rearrangement, in which large gene families of complete open reading frames can reassort by inversion so as to vary the surface protein expression of the microbe.

EXAMPLE 19

Mutant *C. fetus* Strain with Cassettes Replaced by a Heterologous Antigen

Each of the sapA homologs is altered so that the central portion of the homolog-specific region is replaced by a DNA cassette encoding a heterologous antigen. Representative examples of cassettes that can be inserted are immunogens related to Salmonella, *Campylobacter jejuni*, *E. coli* 0157:H7, human immunodeficiency virus (HIV), simian immunodeficiency virus (SIV) as well as venereal, gastrointestinal, or respiratory pathogens of humans, cattle, sheep, poultry, horses, swine, and reptiles. The replacement is constructed so that the encoded S-layer protein is a tripartite chimera consisting of the N-terminal LPS-bining domain of the S-layer protein, a central region composed of the heterologous antigen, and a C-terminal segment containing the S-layer protein secretion signal. This protein would be able to be secreted from the cell by means of the C-terminal secretion signal and into the LPS on the *C. fetus* cell surface, thereby exposing the heterologous antigen to the host immune system. Because the natural cassettes are replaced by the chimerae, one embodiment of the invention is the expectation that carriage of this organism is substantially shorter than for the wild type strain and thus, self-limiting. This strain should colonize for less than 3 months allowing the host to develop a mucosal and systemic immune response to each of the immunogens.

In another embodiment, one may use a mutant *C. fetus* strain in which all but one of the cassettes is replaced by a heterologous antigen. This embodiment is similar to Example 12 except that one of the cassettes (e.g., sapA2) remains in its native configuration but that the others are mutagenized to form chimerae. The advantage of this construction is that one can induce immunity to *C. fetus* based on the single full-length S-Layer protein produced.

EXAMPLE 20

Mutant *C. fetus* Strain in Which recA is Mutagenized

In another embodiment of the present invention, one may mutagenize recA so that the RecA protein is not produced and therefore, the DNA rearrangements permitting sapA antigenic variation can not occur at any detectable frequency. Thus, the *C. fetus* strain can only produce one of the S-Layer proteins encoded by one sapA homolog. This strain should only colonize the host briefly, i.e., until protective immunity has developed to that homolog. Subsequently, the host immune response should eliminate the organism. Thus, this mutant would provide effective immunity against subsequent *C. fetus* infection and is useful for vaccination of ungulates (including sheep, cattle and horses) in which infectious abortion and/or infertility can occur after the wild-type infection.

EXAMPLE 21

*C. fetus* Strain in Which recA is Mutagenized and the sapA Homolog That is Being Expressed is a Chimera Involving a Heterologous Peptide In this embodiment, a sapA homolog is mutagenized to allow expression of a chimeric protein including a heterologous antigen. The strain is then passaged in vitro so that the chimeric homolog is in the expression position and then a recA mutation is made. This strain now expresses only the chimeric protein which can serve as a means to immunize a host to that antigen. Since the strain can not vary and is not producing a native S-Layer protein, the duration of colonization in the host is brief (days). This attenuation of the *C. fetus* strain allows safe immunization for the selected antigen.

EXAMPLE 22

Mixed Mutant *C. fetus* Strains Each Including a sapA Chimera Which is Also a recA Mutant In this embodiment, a series of mutants are constructed in which for each a single sapA homolog is mutagenized with the replacement to encode a different chimeric protein, each one representing a different heterologous antigen. Each mutant is also RecA-deficient due to mutation in recA. A host is inoculated with a mixture of two or more of these strains to provide immunization to the requisite antigens. Each strain is short-lived in the immunized host.

EXAMPLE 23

Mutant *C. fetus* Strain That Secretes a Heterologous Antigen

Each of the sapA homologs is altered so that the 5' section of the homolog-specific region is replaced by a DNA cassette encoding a heterologous antigen. Examples of the cassettes that can be inserted are immunogens related to Salmonella, *Campylobacter jejuni*, *E. coli* 0157:H7, human immunoeficiency virus (HIV), simian immunoeficiency virus (SIV) as well as veneral, gastrointestinal, or respiratory pathogens of humans, cattle sheep, poultry, horses, swine, and reptiles. The replacement is constructed so that the encoded S-layer protein is a bipartite chimera consisting a central region composed of the heterologous antigen and a C-terminal segment containing the S-layer protein secretion signal. This protein would be able to be secreted from the cell by means of the C-terminal secretion signal thereby exposing the heterologous antigen to the host immune system. Because the natural cassettes are replaced by the chimerae, one embodiment of the invention is the expectation that carriage of this organism is substantially shorter than for the wild type strain and thus, self-limiting. This strain should colonize for less than 3 months allowing the host to develop a mucosal and systemic immune response to each of the immunogens.

In another embodiment, one may use a mutant *C. fetus* strain in which all but one of the cassettes is replaced by a heterologous antigen. This embodiment is similar to Example 12 except that one of the cassettes (e.g., sapA2) remains in its native configuration but that the others are mutagenized to form chimerae. The advantage of this construction is that one can induce immunity to *C. fetus* based on the single full-length S-Layer protein produced.

The following references were cited herein:
1. Borst, P. & Greaves, D. R. (1982) *Science* 235, 658–667.
2. Fujimoto, et al., (1991) *Infect. Immun.* 59, 2017–2022.
3. Beveridge, T. J., Koval, S. F. (1993) Advances in paracrystalline bacterial surface layers. Plenum Press, New York. 1–344.
4. Blaser, et al., (1988) *J. Clin. Invest.* 81, 1434–1444.
5. Wang, et al., (1993) *J. Bacteriol.* 175, 4979–4984.
6. Garcia, et al., (1995) *J. Bacteriol.* 177, 1976–1980.
7. Dworkin, et al., (1995) *J. Biol. Chem.* 270, 15093–15101.
8. Dworkin, et al., (1995) *J. Bacteriol.* 177, 1734–1741.
9. Dworkin, et al., (1996) *Mol. Microbiol.* 19, 1241–1253.
10. Glasgow, et al., (1989) in *Bacterial DNA inversion systems*, eds. Berg, et al., (ASM, Washington, D.C.), pp. 637–659.
11. van de Putte, et al., (1992) *Trends in Genetics* 8, 457–462.
12. Tummuru, et al., (1992) *J. Bacteriol.* 174, 5916–5922.
13. Blaser, et al., (1987) *J. Infect. Dis.* 155, 696–705.
14. Sambrook, et al., (1989) *Molecular cloning: a laboratory manual*, Cold Spring Harbor Lab., Cold Spring Harbor, N.Y.).
15. Birnboim, et al., (1979) *Nucleic Acids Res.* 7, 1513–1523.
16. Blaser, et al., (1985) *J. Infect. Dis.* 151, 227–235.
17. Wang, E. & Taylor, D. E. (1990) *Gene* 94, 23–28.
18. Trieu-Cout, et al., (1985) *EMBO J.* 4, 3583–3587.
19. Feinberg, et al., (1983) *Anal. Biochem.* 132, 6–13.
20. Pei, Z. & Blaser, M. J. (1990) *J. Clin. Invest.* 85, 1036–1043.
21. Winter, et al., (1978) *Infect. Immun.* 22, 963–971.
22. Blaser, M. J. & Pei, Z. (1993) *J. Infect. Dis.* 167, 696–706.
23. Blaser, et al., (1990) *J. Biol. Chem.* 265, 14529–14535.
24. Tummuru, M. K. R. & Blaser, M. J. (1993) *Proc. Natl. Acad. Sci. USA*. 90, 7265–7269.
25. Gellert, M. & Nash, H. (1987) *Nature (London)* 325, 401–404.
26. Silverman, et al., (1979) *Proc. Natl. Acad. Sci. USA* 76, 391–395.
27. Abraham, et al., (1985) *Proc. Natl. Acad. Sci. USA* 82, 5724–5727.
28. Marrs, et al., (1988) *J. Bacteriol.* 170, 3032–3039.
29. Iida, et al., (1982) *EMBO J.* 1, 1445–1453.
30. Giphart-Gassler, et al., (1982) *Nature (London)* 297, 339–342.
31. Blaser, et al., (1994) *Mol. Microbiol.* 14, 453–462.
32. Salama, et al., (1992) *Int. J. System. Bacteriol.* 42, 446–450.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A genetically engineered mutant *C. fetus* strain derived from strain 23D which has an ATCC designation PTA-4754, said mutant strain contains a DNA cassette inserted into the coding sequence of a sapA homolog of said 23D strain, wherein said DNA cassette encodes a heterologous protein and expression of said DNA cassette results in surface expression of a chimeric protein comprising a 5' LPS-binding region of said sapA homolog, said heterologous protein and a 3' secretion signal region of said sapA homolog.

2. The mutant *C. fetus* strain of claim 1, wherein said protein is selected from the group consisting of an antigen and a therapeutic agent.

3. The mutant *C. fetus* strain of claim 1, wherein said heterologous protein is an immunogen of a pathogen selected from the group consisting of Salmonella, Shigella, *Campylobacter jejuni, E. coli* 0157:H7, human immunodeficiency virus (HIV), and simian immunodeficiency virus (SIV).

4. A method of immunizing a host to develop mucosal and systemic immune responses to an immunogen carried by the mutant strain of claim 3, comprising the step of administering to said host the mutant strain of claim 3.

5. A mutant *C. fetus* strain derived from recA mutant strain 97-211 which has an ATCC designation PTA-4753, said mutant *C. fetus* strain expresses only one S-layer protein encoded by one sapA homolog due to a recA mutation that results in no functional RecA protein expression.

6. The mutant *C. fetus* strain of claim 5, wherein a DNA cassette is inserted into the coding sequence of said sapA homolog, said DNA cassette encodes a heterologous protein and expression of said DNA cassette results in surface expression of a chimeric protein comprising a 5' LPS-binding region of said sapA homolog, said heterologous protein and a 3' secretion signal region of said sapA homolog.

7. A method of immunizing a host to develop mucosal and systemic immune responses to the heterologous protein carried by the mutant strain of claim 6, comprising the step of administering to said host the mutant strains of claim 6.

8. A mixture of mutant *C. fetus* strains derived from recA mutant strain 97-211 which has an ATCC designation PTA-4753, wherein due to recA mutation there is no functional RecA protein expression in each of said strains, each of said strains comprises a DNA cassette inserted into the coding sequence of a sapA homolog of said strain, said DNA cassette encodes a different heterologous protein in each of said mutant strains and expression of said DNA cassette results in surface expression of a chimeric protein comprising a different heterologous protein in each of said mutant strains.

9. A strain of *Escherichia coli* having an ATCC designation PTA-4750 modified to express the surface array proteins C, D, E and F of *C. fetus* strain 23D, wherein said surface array proteins are encoded by the pIR100 plasmid contained in said strain of *E. coli.*

10. The *Escherichia coli* of claim 9, further comprises a chimeric protein encoded by sequences comprising a 5' LPS-binding region of a sapA homolog of *C. fetus* strain 23D of ATCC designation PTA-4754, a 3' secretion signal region of said sapA homolog and sequence encoding a heterologous protein inserted between said binding region and said signal region.

11. A method of immunizing a host to generate immune responses to the heterologous protein carried by the *Escherichia coli* of claim 10, comprising the step of administering to said host the *Escherichia coli* of claim 10.

* * * * *

SEQUENCE LISTING

```
<160> NUMBER OF SEQ ID NOS: 20

<210> SEQ ID NO 1
<211> LENGTH: 20
<212> TYPE: DNA
<213> ORGANISM: artificial sequence
<220> FEATURE:
<221> NAME/KEY: primer
<223> OTHER INFORMATION: Forward primer for kanamycin-resistance (km)
      gene cassette

<400> SEQUENCE: 1
tgtagaaaag aggaaggaaa                                              20

<210> SEQ ID NO 2
<211> LENGTH: 20
<212> TYPE: DNA
<213> ORGANISM: artificial sequence
```

```
<220> FEATURE:
<221> NAME/KEY: primer
<223> OTHER INFORMATION: Reverse primer for kanamycin-resistance (km)
      gene cassette

<400> SEQUENCE: 2
ctaaaacaat tcatccagta                                                    20

<210> SEQ ID NO 3
<211> LENGTH: 24
<212> TYPE: DNA
<213> ORGANISM: artificial sequence
<220> FEATURE:
<221> NAME/KEY: primer
<223> OTHER INFORMATION: Forward primer for chloramphenicol-resistance
      (cm) gene cassette

<400> SEQUENCE: 3
agtggataga tttatgatat agtg                                               24

<210> SEQ ID NO 4
<211> LENGTH: 22
<212> TYPE: DNA
<213> ORGANISM: artificial sequence
<220> FEATURE:
<221> NAME/KEY: primer
<223> OTHER INFORMATION: Reverse primer for chloramphenicol-resistance
      (cm) gene cassette

<400> SEQUENCE: 4
tttatttatt cagcaagtct tg                                                 22

<210> SEQ ID NO 5
<211> LENGTH: 20
<212> TYPE: DNA
<213> ORGANISM: artificial sequence
<220> FEATURE:
<221> NAME/KEY: primer
<223> OTHER INFORMATION: Forward primer for middle sapA promoter region

<400> SEQUENCE: 5
catctctaca gcagcaaaag                                                    20

<210> SEQ ID NO 6
<211> LENGTH: 24
<212> TYPE: DNA
<213> ORGANISM: artificial sequence
<220> FEATURE:
<221> NAME/KEY: primer
<223> OTHER INFORMATION: Forward primer for sapA promoter region

<400> SEQUENCE: 6
gcggagataa tgttgtagtt gatg                                               24

<210> SEQ ID NO 7
<211> LENGTH: 21
<212> TYPE: DNA
<213> ORGANISM: artificial sequence
<220> FEATURE:
<221> NAME/KEY: primer
<223> OTHER INFORMATION: Reverse primer for sapA promoter region

<400> SEQUENCE: 7
aactttaaga tctagcgtac c                                                  21

<210> SEQ ID NO 8
<211> LENGTH: 21
```

```
<212> TYPE: DNA
<213> ORGANISM: artificial sequence
<220> FEATURE:
<221> NAME/KEY: primer
<223> OTHER INFORMATION: Forward primer for middle sapA1 promoter
      region

<400> SEQUENCE: 8
agggtactga tttagacgat a                                              21

<210> SEQ ID NO 9
<211> LENGTH: 24
<212> TYPE: DNA
<213> ORGANISM: artificial sequence
<220> FEATURE:
<221> NAME/KEY: primer
<223> OTHER INFORMATION: Forward primer for 3'sapA1 promoter region

<400> SEQUENCE: 9
gctggattta caggagattt aacc                                           24

<210> SEQ ID NO 10
<211> LENGTH: 27
<212> TYPE: DNA
<213> ORGANISM: artificial sequence
<220> FEATURE:
<221> NAME/KEY: primer
<223> OTHER INFORMATION: Reverse primer #1 for 3'sapA1 promoter region

<400> SEQUENCE: 10
gttactggta tcaataacaa cataagt                                        27

<210> SEQ ID NO 11
<211> LENGTH: 21
<212> TYPE: DNA
<213> ORGANISM: artificial sequence
<220> FEATURE:
<221> NAME/KEY: primer
<223> OTHER INFORMATION: Reverse primer #2 for 3'sapA1 promoter region

<400> SEQUENCE: 11
ctacgtaatc atactgctac c                                              21

<210> SEQ ID NO 12
<211> LENGTH: 15
<212> TYPE: DNA
<213> ORGANISM: Campylobacter fetus
<220> FEATURE:
<223> OTHER INFORMATION: Palindromic sequence of putative recombinase
      recognition site present in the 5' conserved
      region of S-layer protein gene cassette

<400> SEQUENCE: 12
ttaaggaatc cttaa                                                     15

<210> SEQ ID NO 13
<211> LENGTH: 8
<212> TYPE: PRT
<213> ORGANISM: Campylobacter fetus
<220> FEATURE:
<222> LOCATION: 365..377
<223> OTHER INFORMATION: Amino acid sequence motif of ATP/GTP binding
      site of SapD protein

<400> SEQUENCE: 13

Gly Pro Ser Ala Ala Gly Lys Ser
                5
```

```
<210> SEQ ID NO 14
<211> LENGTH: 12
<212> TYPE: PRT
<213> ORGANISM: Campylobacter fetus
<220> FEATURE:
<222> LOCATION: 468..479
<223> OTHER INFORMATION: Amino acid sequence motif of peptide that is a
      signature sequence for ABC transporters found in
      SapD protein

<400> SEQUENCE: 14

Lys Ser Gly Gly Gln Arg Gln Arg Val Ala Leu Ala
                  5                  10

<210> SEQ ID NO 15
<211> LENGTH: 5
<212> TYPE: PRT
<213> ORGANISM: Campylobacter fetus
<220> FEATURE:
<223> OTHER INFORMATION: Amino acid sequence of conserved peptide found
      in SapA, SapA1, and SapB protein C-termini; Xaa = Thr
      or Gly at position #5

<400> SEQUENCE: 15

Gly Asp Gly Ser Xaa
                  5

<210> SEQ ID NO 16
<211> LENGTH: 5
<212> TYPE: PRT
<213> ORGANISM: Campylobacter fetus
<220> FEATURE:
<223> OTHER INFORMATION: Amino acid sequence of conserved peptide
      found in SapA2 protein C-terminus

<400> SEQUENCE: 16

Ser Lys Gly Ser Thr
                  5

<210> SEQ ID NO 17
<211> LENGTH: 8
<212> TYPE: PRT
<213> ORGANISM: Campylobacter fetus
<220> FEATURE:
<223> OTHER INFORMATION: Amino acid sequence of conserved peptide found
      in SapA, SapA1, and SapB protein C-termini; Xaa = unknown
      at position #2; Xaa = Val or Ile at position #7

<400> SEQUENCE: 17

Gly Xaa Thr Tyr Val Val Xaa Asp
                  5

<210> SEQ ID NO 18
<211> LENGTH: 8
<212> TYPE: PRT
<213> ORGANISM: Campylobacter fetus
<220> FEATURE:
<223> OTHER INFORMATION: Amino acid sequence of conserved peptide found
      in SapA2 protein C-terminus; Xaa = unknown at position #2

<400> SEQUENCE: 18

Gly Xaa Thr Tyr Val Val Asp Ala
                  5

<210> SEQ ID NO 19
<211> LENGTH: 4
<212> TYPE: PRT
<213> ORGANISM: unknown
```

-continued

```
<220> FEATURE:
<223> OTHER INFORMATION: Amino acid sequence of motif implicated in
      protease secretion

<400> SEQUENCE: 19

Asp Val Ile Val
 1

<210> SEQ ID NO 20
<211> LENGTH: 5
<212> TYPE: PRT
<213> ORGANISM: Campylobacter fetus
<220> FEATURE:
<223> OTHER INFORMATION: Amino acid sequence similar to protease
      secretion motif found in SapA and SapB protein C-termini

<400> SEQUENCE: 20

Asp Gly Ser Val Ile
                5
```